US006057269A

United States Patent [19]
Klintz et al.

[11] Patent Number: 6,057,269

[45] Date of Patent: May 2, 2000

[54] BENZYLHYDROXYLAMINES AND INTERMEDIATES USED TO PREPARE THEM

[75] Inventors: Ralf Klintz, Grünstadt; Gerhard Hamprecht, Weinheim; Elisabeth Heistracher, Mannheim; Peter Schäfer, Ottersheim; Cyrill Zagar, Ludwigshafen; Karl-Otto Westphalen, Speyer; Helmut Walter, Obrigheim; Ulf Misslitz, Neustadt; Olaf Menke, Altleiningen; Markus Menges, Mannheim, all of Germany

[73] Assignee: BASF Aktiengesellschaft, Ludwigshafen, Germany

[21] Appl. No.: 08/973,780

[22] PCT Filed: Jun. 27, 1996

[86] PCT No.: PCT/EP96/02805

§ 371 Date: Jan. 5, 1998

§ 102(e) Date: Jan. 5, 1998

[87] PCT Pub. No.: WO97/02253

PCT Pub. Date: Jan. 23, 1997

[30] Foreign Application Priority Data

| | | | |
|---|---|---|---|
| Jul. 6, 1995 | [DE] | Germany | 195 24 617 |
| Apr. 26, 1996 | [DE] | Germany | 196 16 719 |

[51] Int. Cl.[7] .................... C07D 239/54; C07C 265/12; C07C 239/20; A01N 43/54

[52] U.S. Cl. .................... 504/243; 504/168; 504/229; 504/230; 504/236; 544/238; 544/295; 544/296; 544/180; 544/182; 544/300; 544/301; 544/310; 544/311; 544/312; 549/476; 560/20; 560/24; 560/32; 560/34; 560/358; 558/417; 564/34; 564/49; 564/51; 564/300

[58] Field of Search .................... 504/168, 243; 544/300, 301, 310, 311, 312; 560/20, 24, 32, 34, 358; 564/51, 300, 49, 34; 558/417; 549/476

[56] References Cited

U.S. PATENT DOCUMENTS

| | | | |
|---|---|---|---|
| 5,336,663 | 8/1994 | Wenger et al. | 504/243 |
| 5,486,521 | 1/1996 | Brouwer et al. | 514/274 |
| 5,700,805 | 12/1997 | Schafer et al. | 514/269 |

FOREIGN PATENT DOCUMENTS

| | | |
|---|---|---|
| 408 382 | 1/1991 | European Pat. Off. . |
| 4237920 | 11/1992 | Germany . |
| 87/04049 | 7/1987 | WIPO . |
| 93/06090 | 4/1993 | WIPO . |
| 95/06641 | 3/1995 | WIPO . |

*Primary Examiner*—Mukund J. Shah
*Assistant Examiner*—Ann M. Kessinger
*Attorney, Agent, or Firm*—Keil & Weinkauf

[57] ABSTRACT

Benzylhydroxylamines I

I

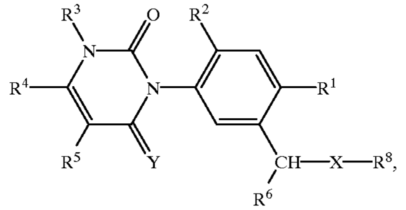

($X$=—N($R^7$)—O—; Y=O, S;

$R^1$=halogen, CN, $NO_2$, $CF_3$; $R^2$=H, halogen; $R^3$=H, $NH_2$, $CH_3$;

$R^4$=H, halogen, $C_1$–$C_6$-alkyl, $C_1$–$C_6$-haloalkyl, $C_1$–$C_6$-alkylthio, $C_1$-$C_6$-alkylsulfinyl or $C_1$–$C_6$-alkylsulfonyl;

$R^5$=H, halogen, $C_1$–$C_6$-alkyl;

$R^6$=H, $C_1$–$C_6$-alkyl, $C_1$–$C_6$-haloalkyl, $C_3$-$C_6$-cycloalkyl, $C_2$–$C_6$-alkenyl;

$R^7$=H, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, $C_1$–$C_6$-alkylcarbonyl, $C_3$–$C_6$-alkenylcarbonyl, $C_3$–$C_6$-alkynylcarbonyl, $C_1$–$C_6$-alkoxycarbonyl, $C_2$–$C_8$-alkenyloxycarbonyl, $C_2$–$C_6$-alkynyloxycarbonyl, $C_1$–$C_6$-alkylthiocarbonyl, $C_1$–$C_6$-alkylsulfonyl, $C_1$–$C_6$-alkylcarbamoyl, it being possible for the 14 last-mentioned radicals to have attached to them 1–3 substituents:

$NO_2$, CN, halogen, $C_3$–$C_8$-cycloalkyl, OH, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylcarbonyl, $C_1$–$C_6$-alkylcarbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, unsubstituted or substituted phenyl, phenoxy or phenylsulfonyl, a 3- to 7-membered heterocyclyl or heterocyclyloxy group having 1–3 hetero atoms, it being possible for this group to be saturated, unsaturated or aromatic and to have attached to it 1–3 substituents, —CO—$Z^1R^9$, —OCO—$Z^1R^9$, —N($R^9$)$R^{10}$ or $R^7$=unsubstituted or substituted cycloalkylcarbonyl, phenylcarbonyl, phenylsulfonyl, phenylcarbamoyl;

$R^8$=H, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, it being possible for each of the 5 last-mentioned radicals to have attached to it 1–3 substituents:

$NO_2$, CN, halogen, $C_3$–$C_8$-cycloalkyl, OH, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, unsubstituted or substituted phenyl- [sic], phenoxy- [sic] or phenylsulfonyl, a 3- to 7-membered heterocyclyl or heterocyclyloxy group having 1–3 hetero atoms, it being possible for this group to be saturated, unsaturated or aromatic and to have attached to it 1–3 substituents,

—CO—$Z^2R^{11}$, —OCO—$Z^2R^{11}$, —N($R^{11}$)$R^{12}$;

$Z^1$ a chemical bond, oxygen, sulfur or —N($R^{10}$)—;

$Z^2$=a chemical bond, oxygen, sulfur or —N($R^{12}$)—;

$R^9$, $R^{11}$=H, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, unsubstituted or substituted phenyl or phenyl-$C_1$–$C_6$-alkyl, or $Z^1$ and $R^9$ and/or $Z^2$ and $R^{11}$ together=a 3- to 7-membered heterocycle having 1–3 hetero atoms and bonded via nitrogen, it being possible for this heterocycle to be saturated, unsaturated or aromatic and, if desired, to have attached to it one to three substituents, $R^{10}$, $R^{12}$=H, OH, $C_1$–$C_6$-alkyl, $C_3$–$C_8$-cycloalkyl, $C_1$–$C_6$-alkoxy)

and the salts of I where $R^3$, $R^7$ and/or $R^8$=hydrogen are used as herbicides and for the desiccation/defoliation of plants.

15 Claims, No Drawings

BENZYLHYDROXYLAMINES AND INTERMEDIATES USED TO PREPARE THEM

The present invention relates to novel benzylhydroxylamines of the general formula I

I

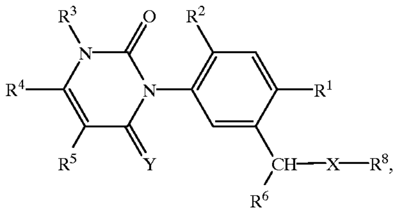

in which the variables have the following meanings:

X is —N($R^7$)—O— which can be bonded to $R^8$ via oxygen or nitrogen;

Y is oxygen or sulfur;

$R^1$ is halogen, cyano, nitro or trifluoromethyl;

$R^2$ is hydrogen or halogen;

$R^3$ is hydrogen, amino or methyl;

$R^4$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;

$R^5$ is hydrogen, halogen or $C_1$–$C_6$-alkyl;

$R^6$ is hydrogen, $C_1$–$C_6$-alkyl, $C_1$–$C_6$-haloalkyl, $C_3$–$C_6$-cycloalkyl or $C_2$–$C_6$-alkenyl;

$R^7$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_2$–$C_6$-alkenyloxy)carbonyl, ($C_2$–$C_6$-alkynyloxy)carbonyl, ($C_1$–$C_6$-alkylthio)carbonyl, $C_1$–$C_6$-alkylsulfonyl, $C_1$–$C_6$-alkylcarbamoyl, it optionally being possible for each of the last-mentioned 14 radicals to have attached to it one to three substituents in each case selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl) carbonyl, ($C_1$–$C_6$-alkyl) carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, the phenyl, phenoxy or phenylsulfonyl group, it being possible for the phenyl rings to be unsubstituted or to have attached to them one to three substituents, in each case selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, it being possible for the heterocycle to be saturated, partially or fully unsaturated or aromatic, and, if desired, to have attached to it one to three substituents, in each case selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^1R^9$, —OCO—$Z^1R^9$ or —N($R^9$)$R^{10}$, or $R^7$ is $C_3$–$C_8$-cycloalkylcarbonyl, phenylcarbonyl, phenylsulfonyl or phenylcarbamoyl, it being possible for these 4 radicals to be unsubstituted or to have attached to them one to three substituents, in each case selected from the group consisting of halogen, nitro, cyano, $C_1$–$C_6$-alkyl, $C_1$–$C_6$-alkoxy and $C_1$–$C_6$-haloalkyl;

$R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, it optionally being possible for each of the last-mentioned 5 radicals to have attached to it one to three substituents, in each case selected from the group consisting of nitro, cyano, halogen, $C_3$–$C_8$-cycloalkyl, hydroxyl, $C_1$-$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, the phenyl, phenoxy or phenylsulfonyl group, it being possible for the phenyl rings to be unsubstituted or to have attached to them one to three substituents, in each case selected from the group consisting of nitro, cyano, halogen, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, it being possible for the heterocycle to be saturated, partially or fully unsaturated or aromatic, and, if desired, to have attached to it one to three substituents, in each case selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^2R^{11}$, —OCO—$Z^2R^{11}$ or —N($R^{11}$)$R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, it being possible for the phenyl group and the phenyl ring of the phenylalkyl group to be unsubstituted or to have attached to them one to three radicals, in each case selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl) carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, it being possible for the heterocycle to be saturated, partially or fully unsaturated or aromatic and, if desired, to have attached to it one to three substituents in each case selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy, and the agriculturally useful salts of those compounds I where $R^3$, $R^7$ and/or $R^8$ are hydrogen.

Furthermore, the invention relates to the use of the compounds I as herbicides or for the desiccation and/or defoliation of plants, herbicidal compositions and compositions for the desiccation and/or defoliation of plants which comprise the compounds I as active ingredients, methods of controlling undesirable vegetation and for the desiccation and/or defoliation of plants using the compounds I, processes for the preparation of herbicidal compositions and compositions for the desiccation and/or defoliation of plants using the compounds I, and novel intermediates of the formulae IV, V, XIII, XVI, XVII, XIX and XXIII, from which the compounds I can be obtained.

WO 93/06090 and EP-A 408 382 have already described certain 3-phenyluracils as herbicides and for the desiccation/defoliation of plants which—with a suitable choice of substituents—differ from the present compounds I especially by the fact that the phenyl ring has attached to it an iminomethyl group instead of the substituent —$CH(R^6)$—X—$R^8$.

In accordance with WO 95/06641, other compounds which are also suitable as herbicides and for the desiccation/defoliation of plants are, inter alia, those of the formula II

II

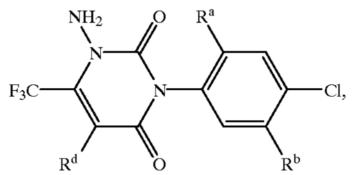

where $R^a$ is hydrogen, fluorine or chlorine and $R^b$ is, inter alia, a hydroxyiminomethyl or oxyiminomethyl group.

Finally, DE-A 42 37 920 discloses that certain 3-aryluracils, inter alia the compounds of the formula III

III

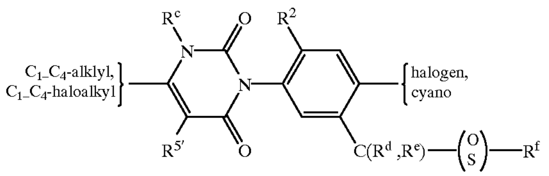

where $R^c$ is hydrogen, $C_1$–$C_4$-alkyl, $C_1$–$C_4$-haloalkyl, $C_3/C_4$-alkenyl or $C_3/C_4$-alkynyl;

$R^d$ and $R^e$ are hydrogen, $C_1$–$C_8$-alkyl, $C_3$–$C_7$-cycloalkyl or $C_3$–$C_7$-cycloalkyl-$C_1$–$C_4$-alkyl;

$R^f$ is hydrogen, $C_1$–$C^5$-alkyl, $C_1$–$C_4$-alkoxy-$C_1$–$C_4$-alkyl, $C_3$–$C_8$-cycloalkyl, $C_3$–$C_8$-cycloalkyl-$C_1$–$C_4$-alkyl, $C_1$–$C_5$-haloalkyl, $C_2$–$C_5$-alkenyl, $C_2$–$C_5$-alkynyl, unsubstituted or substituted aryl or benzyl, or is a keto, ester or thioester group, and $R^{5'}$ is hydrogen, halogen or $C_1$–$C_4$-alkyl are suitable for controlling weeds.

However, the herbicidal properties of the known compounds are not always entirely satisfactory. Accordingly, it was an object of the present invention to provide novel, in particular herbicidally active, compounds with which undesirable plants can be subjected to better targeted control than was possible to date.

Another object was to provide novel compounds with a desiccant/defoliant action.

Accordingly, we have found that this object is achieved by the benzylhydroxylamines of the formula I and their herbicidal action.

Furthermore, there have been found herbicidal compositions which comprise the compounds I and which have a very good herbicidal action. Moreover, there have been found processes for the preparation of these compositions and methods of controlling undesirable vegetation using the compounds I.

Furthermore, it has been found that the compounds I are also suitable for the defoliation and desiccation of parts of plants, suitable plants being crop plants such as cotton, potatoes, oilseed rape, sunflowers, soya beans or field beans, in particular cotton. In this respect, there have been found compositions for the desiccation and/or defoliation of plants, processes for the preparation of these compositions, and methods for the desiccation and/or defoliation of plants using the compounds I.

Depending on their substitution pattern, the compounds of the formula I can contain one or more chiral centers, in which case they are present as enantiomer or diastereomer mixtures. The present invention relates to the pure enantiomers or diastereomers and also to mixtures of these.

If $R^3$, $R^7$ and/or $R^8$ are hydrogen, the benzylhydroxylamines I can be present in the form of their agriculturally useful salts, the nature of the salt generally not being critical. In general, suitable salts are salts of those bases which do not adversely affect the herbicidal action in comparison with the free compound I.

Particularly suitable basic salts are the salts of the alkali metals, preferably sodium and potassium salts, of the alkaline earth metals, preferably calcium and magnesium salts, those of the transition metals, preferably zinc and iron salts, and ammonium salts where the ammonium ion may, if desired, have attached to it one to four $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium- and trimethyl(2-hydroxyethyl) ammonium salts, furthermore phosphonium salts, sulfonium salts, such as, preferably, tri($C_1$–$C_4$-alkyl)sulfonium salts, and sulfoxonium salts such as, preferably, tri($C_1$–$C_4$-alkyl) sulfoxonium salts.

The organic moieties mentioned for the substituents $R^4$ to $R^{12}$ or as radicals on phenyl rings or heterocycles are collective terms for individual enumerations of the individual members of the groups. All carbon chains, i.e. all alkyl, haloalkyl, alkoxy, alkylthio, alkylsulfenyl [sic], alkylsulfonyl, alkylcarbonyl, alkoxycarbonyl, alkenyl, alkenyloxy, alkenylcarbonyl, alkynyl, alkynyloxy, alkynylcarbonyl and alkylideneaminooxy moieties can be straight-chain or branched. Unless otherwise specified, halogenated substituents preferably have attached to them one to five identical or different halogen atoms. The meaning halogen is in each case fluorine, chlorine, bromine or iodine.

Other examples of meanings are $C_1$–$C_4$-alkyl and the alkyl moieties of ($C_1$–$C_6$-alkyl)carbonyl, ($C_1$–$C_6$-alkyl)carbonyloxy, $C_1$–$C_6$-alkylcarbamoyl, $C_1$–$C_6$-alkoxy-$C_1$–$C_6$-alkyl and ($C_1$–$C_6$-alkoxy)carbonyl-$C_1$–$C_6$-alkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropl [sic], 1,2,2-trimethylpropyl, 1-ethyl-1-methylpropyl or 1-ethyl-2-methylpropyl;

$C_1$–$C_6$-haloalkyl: a $C_1$–$C_6$-alkyl radical as mentioned above which is partially or fully substituted by fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, petafluoroethyl [sic], 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

phenyl-$C_1$–$C_6$-alkyl: e.g. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)eth-1-yl, 1-(phenylmethyl)-1-(methyl)-eth-1-yl or 1-(phenylmethyl)prop-1-yl, preferably benzyl, 2-phenylethyl or 2-phenyl-hex-6-yl;

$C_3$–$C_6$-alkenyl and the alkenyl moieties of $C_3$–$C_6$-alkenyloxy and ($C_3$–$C_6$-alkenyl)carbonyl: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl or 2-methylprop-2-en-1-yl, n-penten-1-yl, n-penten-2-yl, n-penten-3-yl, n-penten-4-yl, 1-methyl-but-1-en-1-yl, 2-methylbut-1-en-1-yl, 3-methylbut-1-en-1-yl, 1-methylbut-2-en-1-yl, 2-methylbut-2-en-1-yl, 3-methyl-but-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-mmethylpent-1-en-1-yl [sic], 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylput-3-en-1-yl [sic], 1,2-dimethylbut-1-en-1-yl, 1,2-dimetylput-2-en-1-yl [sic], 1,2-dimethylbut-3-en-1-yl, 1,3-dimetylput-1-en-1-yl [sic], 1,3-dimethylbut-2-en-1-yl, 1,3-dimetylput-3-en-1-yl [sic], 2,2-dimethylbut-3-en-1-yl, 2,3-dimetylput-1-en-1-yl [sic], 2,3-dimethylbut-2-en-1-yl, 2,3-dimetylput-3-en-1-yl [sic], 3,3-dimethylbut-1-en-1-yl, 3,3-dimetylput-2-en-1-yl [sic], 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$–$C_6$-alkynyl and the alkynyl moieties of $C_3$–$C_6$-alkynyloxy and ($C_3$–$C_6$-alkynyl)carbonyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_2$–$C_6$-alkenyl and the akenyl [sic] moiety of ($C_2$–$C_6$-alkenyloxy)carbonyl: vinyl or one of the radicals mentioned for $C_3$–$C_6$-alkenyl;

the alkynyl moiety of ($C_2$–$C_6$-alkynyloxy)carbonyl: ethynyl or one of the radicals mentioned for $C_3$–$C_6$-akynyl [sic];

$C_1$–$C_6$-alkoxy and the alkoxy moieties of $C_1$–$C_6$-alkoxy-$C_1$–$C_6$-alkyl, ($C_1$–$_6$-alkoxy)carbonyl and ($C_1$–$C_6$-alkoxy)carbonyl-$C_1$–$C_6$-alkyl: methoxy, ethoxy, n-propoxy, 1-methylethoxy, n-butoxy, 1-methylpropoxy, 2-methylpropoxy or 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy,1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_6$-alkylthio and the alkylthio moiety of ($C_1$–$_6$-alkylthio)carbonyl: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1- dimethylpropylsulfinyl, 1,2-dimethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylproplsulfinyl [sic], 1,2,2-trimethylpropylsulfinyl, 1-ethyl-1-methylpropylsulfinyl or 1-ethyl-2-methylpropylsulfinyl;

$C_1$–$C_6$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-alkylideneaminoxy: acetylideneaminoxy, 1-propylideneaminoxy, 2-propylideneaminoxy, 1-butylideneaminoxy, 2-butylideneaminoxy or 2-hexylideneaminoxy;

$C_3$–$C_6$-cycloalkyl: cyclopropyl, cyclobutyl, cyclopentyl or hexyl;

$C_3$–$C_8$-cycloalkyl: cyclopropyl, cyclobutyl, cyclopentyl, cyclohexyl, cycloheptyl or cyclooctyl;

$C_3$–$C_8$-cycloalkoxy: cyclopropyloxy, cyclobutyloxy, cyclopentyloxy, cyclohexyloxy, cycloheptyloxy or cyclooctyloxy.

Examples of 3- to 7-membered heterocycles are oxiranyl, aziridiny [sic], oxetanyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, dioxolanyl, such as 1,3-dioxolan-2-yl and 1,3-dioxolan-4-yl, dioxanyl, such as 1,3-dioxan-2-yl and 1,3-dioxan-4-yl, dithianyl, such as 1,3-dithian-2-yl, furthermore 1,2,4-oxadiazolidinyl, 1,3,4-oxadiazolidinyl, 1,2,4-thiadiazolidinyl, 1,3,4-thiadiazolidinyl, 1,2,4-triazolidinyl, 1,3,4-triazolidinyl, 2,3-dihydrofuryl, 2,5-dihydrofuryl, 2,3-dihydrothienyl, 2,5-dihydrothienyl, 2,3-pyrrolinyl, 2,5-pyrrolinyl, 2,3-isoxazolinyl, 3,4-isoxazolinyl, 4,5-isoxazolinyl, 2,3-isothiazolinyl, 3,4-isothiazolinyl, 4,5-isothiazolinyl, 2,3-dihydropyrazolyl, 3,4-dihydropyrazolyl, 4,5-dihydropyrazolyl, 2,3-dihydrooxazolyl, 3,4-dihydrooxazolyl, piperidinyl, tetrahydropyridazinyl, tetrahydropyrimidinyl, tetrahydropyrazinyl, 1,3,5-tetrahydrotriazinyl and 1,2,4-tetrahydrotriazinyl, and the following heteroaromatic compounds: furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

All phenyl and heterocyclic rings are preferably unsubstituted or have attached to them a halogen, methyl, trifluoromethyl or methoxy substituent.

With a view to the use of the compounds of the formula I according to the invention as herbicides and/or as compounds with a defoliant/desiccant action, the variables preferably have the following meanings, and was [sic] in each case alone or in combination:

X is —N($R^7$)—O— bonded to $R^8$ via oxygen;

X is —O—N($R^7$)— bonded to $R^8$ via nitrogen;

Y is oxygen;

$R^1$ is halogen or cyano;

$R^2$ is hydrogen, fluorine or chlorine;

$R^3$ is amino or methyl;

$R^4$ is $C_1$–$C_6$-alkyl, $C_1$–$C_6$-haloalkyl or $C_1$–$C_6$-alkylsulfonyl, particularly preferably $C_1$–$C_4$-haloalkyl, in particular trifluoromethyl, chlorodifluoromethyl or pentafluoroethyl;

$R^5$ is hydrogen or halogen;

$R^6$ is hydrogen or $C_1$–$C_4$-alkyl, particularly preferably hydrogen;

$R^7$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_2$–$C_6$-alkenyloxy)carbonyl, ($C_2$–$C_6$-alkynyloxy)carbonyl, ($C_1$–$C_6$-alkylthio)carbonyl, $C_1$–$C_6$-alkylcarbamoyl, it being possible, if desired, for each of the last-mentioned 13 radicals to have attached to it one or two substituents, in each case selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, a group —CO—$Z^1R^9$, —OCO—$Z^1R^9$ or —N($R^9$)$R^{10}$;

$R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, it being possible, if desired, for each of the last-mentioned 5 radicals to have attached to it one or two substituents, in each case selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, a group —CO—$Z^2R^{11}$, —OCO—$Z^2R^{11}$ or —N($R^{11}$)$R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl or ($C_1$–$C_6$-alkoxy)carbonyl-$C_1$–$C_6$-alkyl;

or $Z^1$ and $R^9$ and/or $Z^2$ and $R^{11}$ in each case together represent a 3- to 7-membered heterocycle bonded via nitrogen which has one to three hetero atoms selected from the group consisting of two oxygen atoms, two sulfur atoms and 3 nitrogen atoms, it being possible for the heterocycle to be saturated, partially or fully unsaturated or aromatic and, if desired, to have attached to it one to three substituents, in each case selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen or $C_1$–$C_6$-alkyl.

$R^7$ is particularly preferably: hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl or $C_1$–$C_6$-alkylcarbamoyl, it being possible for each of the last-mentioned 10 radicals additionally to have attached to it one of the following substituents: nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfenyl [sic], $C_1$–$C_6$-alkylsulfonyl, $C_1$–$C_6$-alkylideneaminoxy, a group —CO—$Z^1R^9$, —OCO—$Z^1R^9$ or —N($R^9$)$R^{10}$.

$R^8$ is particularly preferably: hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, it being possible for each of the last-mentioned 5 radicals additionally to have attached to it one of the following substituents: nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, a group —CO—$Z^2R^{11}$, —OCO—$Z^2R^{11}$ or —N($R^{11}$)$R^{12}$.

Very particularly preferred are the compounds Ia ($\hat{=}$ I where X=—NH—O—, Y=oxygen, $R^1$=chlorine, $R^2$=fluorine, $R^3$=amino, $R^4$=trifluoromethyl and $R^5$, $R^6$=hydrogen) which are listed in Table 1 below:

TABLE 1

Ia

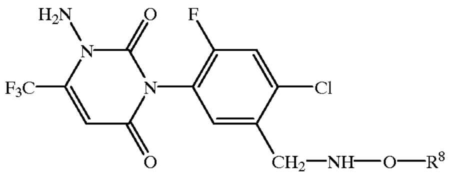

| No. | $R_8$ |
|---|---|
| Ia.01 | H |
| Ia.02 | $CH_3$ |
| Ia.03 | $C_2H_5$ |
| Ia.04 | n-$C_3H_7$ |
| Ia.05 | i-$C_3H_7$ |
| Ia.06 | n-$C_4H_9$ |

TABLE 1-continued

Ia

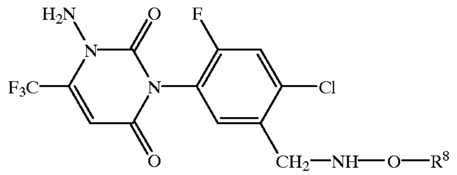

| No. | $R_8$ |
|---|---|
| Ia.07 | i-$C_4H_9$ |
| Ia.08 | s-$C_4H_9$ |
| Ia.09 | tert-$C_4H_9$ |
| Ia.10 | cyclopropyl |
| Ia.11 | cyclobutyl |
| Ia.12 | cyclopentyl |
| Ia.13 | cyclohexyl |
| Ia.14 | cycloheptyl |
| Ia.15 | cyclooctyl |
| Ia.16 | $CH_2CN$ |
| Ia.17 | $CH_2CH_2CN$ |
| Ia.18 | $CH(CH_3)CN$ |
| Ia.19 | $C(CH_3)_2CN$ |
| Ia.20 | $C(CH_3)_2CH_2CN$ |
| Ia.21 | $CH_2Cl$ |
| Ia.22 | $CH_2CH_2Cl$ |
| Ia.23 | $CH(CH_3)CH_2Cl$ |
| Ia.24 | $CH_2CF_3$ |
| Ia.25 | $CHCl_2$ |
| Ia.26 | $CF_2Cl$ |
| Ia.27 | $CF_3$ |
| Ia.28 | $C_2F_5$ |
| Ia.29 | $CF_2H$ |
| Ia.30 | $CH_2$—CH=$CH_2$ |
| Ia.31 | $CH(CH_3)CH$=$CH_2$ |
| Ia.32 | $CH_2$—CH=CH—$CH_3$ |
| Ia.33 | $CH_2$—CCH |
| Ia.34 | $CH(CH_3)C{\equiv}CH$ |
| Ia.35 | $C(CH_3)_2C{\equiv}CH$ |
| Ia.36 | $CH_2$-COOH |
| Ia.37 | $CH_2$—CO—$OCH_3$ |
| Ia.38 | $CH_2$—CO—$OC_2H_5$ |
| Ia.39 | $CH_2$—CO—O-(n-$C_3H_7$) |
| Ia.40 | $CH_2$—CO—O-(i-$C_3H_7$) |
| Ia.41 | $CH(CH_3)$—CO—$OCH_3$ |
| Ia.42 | $CH(CH_3)$—CO—$OC_2H_5$ |
| Ia.43 | $CH(CH_3)$—CO—O-(n-$C_3H_7$) |
| Ia.44 | $CH(CH_3)$—CO—O-(i-$C_3H_7$) |
| Ia.45 | $CH_2$—COO—$(CH_2)_2$—$OCH_3$ |
| Ia.46 | CH2—COO—(CH2)2—$OCH_3$ |
| Ia.47 | $CH(CH_3)$—COO—$(CH_2)_2$—$OCH_3$ |
| Ia.48 | $CH(CH_3)$—COO—$(CH_2)_2$—$OC_2H_5$ |
| Ia.49 | $CH_2$—$CONH_2$ |
| Ia.50 | $CH_2$—$CONHCH_3$ |
| Ia.51 | $CH_2$—$CONHC_2H_5$ |
| Ia.52 | $CH_2$—$CON(CH_3)_2$ |
| Ia.53 | $CH(CH_3)$—$CONH_2$ |
| Ia.54 | $CH(CH_3)$—$CONHCH_3$ |
| Ia.55 | $CH(CH_3)$—CONH-cyclopropyl |
| Ia.56 | $CH(CH_3)$—$CONHC_2H_5$ |
| Ia.57 | $CH(CH_3)$—$CON(CH_3)_2$ |
| Ia.58 | $CH_2$—$SCH_3$ |
| Ia.59 | $(CH_2)_2$—$SCH_3$ |
| Ia.60 | $(CH_2)_2$—$SC_2H_5$ |
| Ia.61 | $(CH_2)_2$—SO—$CH_3$ |
| Ia.62 | $(CH_2)_2$—$SO_2$—$CH_3$ |
| Ia.63 | $(CH_2)_2$-cyclopropyl |
| Ia.64 | $(CH_2)_2$-cyclopentyl |
| Ia.65 | $(CH_2)_2$—O—N=$C(CH_3)_2$ |
| Ia.66 | $(CH_2)_3$—O—N=$C(CH_3)_2$ |
| Ia.67 | $(CH_2)_2$—$NO_2$ |
| Ia.68 | $(CH_2)_2$—$NH_2$ |
| Ia.69 | $(CH_2)_2$—$NHCH_3$ |
| Ia.70 | $(CH_2)_2$—$NH(CH_3)_2$ |
| Ia.71 | $CH_2$—$OCH_3$ |
| Ia.72 | $CH(CH_3)$—$OCH_3$ |

TABLE 1-continued

Ia

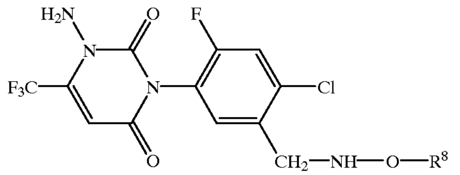

| No. | $R_8$ |
|---|---|
| Ia.73 | $CH(CH_3)—OC_2H_5$ |
| Ia.74 | $CH(CH_3)CH_2—OCH_3$ |
| Ia.75 | $(CH_2)_2OH$ |
| Ia.76 | $CH_2—OC_2H_5$ |
| Ia.77 | $CH_2CO—O—$(4-acetoxytetrahydrofuranyl) |
| Ia.78 | $CH_2—OCOCH_3$ |
| Ia.79 | $CH_2—OCOC_2H_5$ |
| Ia.80 | $CH_2—C_6H_5$ |
| Ia.81 | $(CH_2)_2—C_6H_5$ |
| Ia.82 | $CH_2$-(4-Cl—$C_6H_4$) |
| Ia.83 | $CH_2$-(4-$CF_3$—$C_6H_4$) |
| Ia.84 | $CH_2$-(3-$NO_2$—$C_6H_4$) |

Other very particularly preferred benzylhydroxylamines of the formula I are those which follow:

the compounds Ib.01–Ib.84, which only differ from the corresponding compounds Ia.01–Ia.84 by the fact that $R^1$ is cyano:

Ib

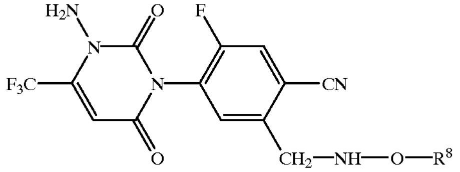

the compounds Ic.01–Ic.84, which only differ from the corresponding compounds Ia.01–Ia.84 by the fact that $R^2$ is hydrogen:

Ic

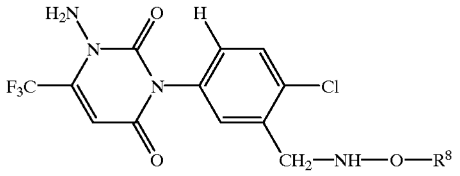

the compounds Id.01–Id.84, which only differ from the corresponding compounds Ia.01–Ia.84 by the fact that $R^1$ is cyano and $R^2$ is hydrogen:

Id

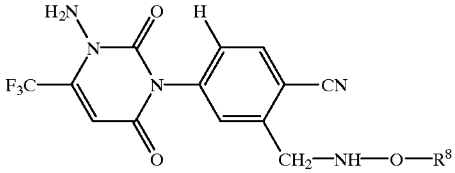

the compounds Ie.01–Ie.84, which only differ from the corresponding compounds Ia.01–Ia.84 by the fact that $R^3$ is methyl:

Ie

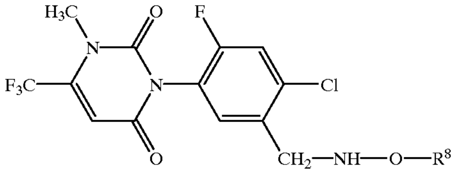

the compounds If.01–If.84, which only differ from the corresponding compounds Ia.01–Ia.84 by the fact that $R^1$ is cyano and $R^3$ is methyl:

If

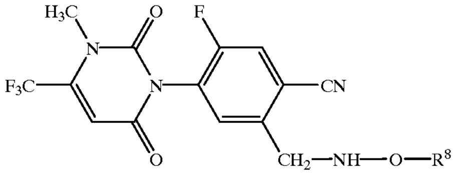

the compounds Ig.01–Ig.84, which only differ from the corresponding compounds Ia.01–Ia.84 by the fact that $R^2$ is hydrogen and $R^3$ is methyl:

Ig

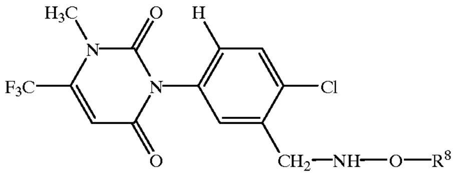

the compounds Ih.01–Ih.84, which only differ from the corresponding compounds Ia.01–Ia.84 by the fact that $R^1$ is cyano, $R^2$ is hydrogen and $R^3$ is methyl:

Ih

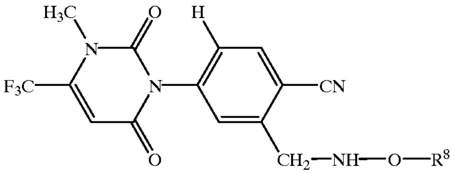

Further very particularly preferred compounds are the compounds Ii (≙ I where Y=oxygen, $R^1$=chlorine, $R^2$=fluorine, $R^3$=amino, $R^4$=trifluoromethyl, $R^5$ and $R^6$=hydrogen, $R^8$=methyl) which are listed in Table 2 below:

TABLE 2

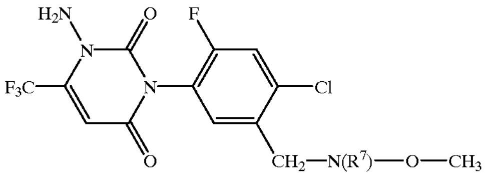

Ii

| No. | $R^7$ |
|---|---|
| Ii.01 | $CH_3$ |
| Ii.02 | $C_2H_5$ |
| Ii.03 | n-$C_3H_7$ |
| Ii.04 | i-$C_3H_7$ |
| Ii.05 | n-$C_4H_9$ |
| Ii.06 | i-$C_4H_9$ |
| Ii.07 | s-$C_4H_9$ |
| Ii.08 | tert-$C_4H_9$ |
| Ii.09 | cyclopropyl |
| Ii.10 | cyclobutyl |
| Ii.11 | cyclopentyl |
| Ii.12 | cyclohexyl |
| Ii.13 | cycloheptyl |
| Ii.14 | cyclooctyl |
| Ii.15 | $CH_2CN$ |
| Ii.16 | $CH_2CH_2CN$ |
| Ii.17 | $CH(CH_3)CN$ |
| Ii.18 | $C(CH_3)_2CN$ |
| Ii.19 | $C(CH_3)_2CH_2CN$ |
| Ii.20 | $CH_2Cl$ |
| Ii.21 | $CH_2CH_2Cl$ |
| Ii.22 | $CH(CH_3)CH_2Cl$ |
| Ii.23 | $CH_2CF_3$ |
| Ii.24 | $CH_2—CH{=}CH_2$ |
| Ii.25 | $CH(CH_3)CH{=}CH_2$ |
| Ii.26 | $CH_2—CH{=}CH—CH_3$ |
| Ii.27 | $CH_2—CCH$ |
| Ii.28 | $CH(CH_3)C{\equiv}CH$ |
| Ii.29 | $C(CH_3)_2C{\equiv}CH$ |
| Ii.30 | $CH_2—COOH$ |
| Ii.31 | $CH_2—CO—OCH_3$ |
| Ii.32 | $CH_2—CO—OC_2H_5$ |
| Ii.33 | $CH_2—CO—O—$(n-$C_3H_7$) |
| Ii.34 | $CH_2—CO$-(i-$C_3H_7$) |
| Ii.35 | $CH(CH_3)—CO—OCH_3$ |
| Ii.36 | $CH(CH_3)—CO—OC_2H_5$ |
| Ii.37 | $CH(CH_3)—CO—O$-(n-$C_3H_7$) |
| Ii.38 | $CH(CH_3)—CO—O$-(i-$C_3H_7$) |
| Ii.39 | $CH_2—COO—(CH_2)_2—OCH_3$ |
| Ii.40 | $CH_2—COO—(CH_2)_2—OCH_3$ |
| Ii.41 | $CH(CH_3)—COO—(CH_2)_2—OCH_3$ |
| Ii.42 | $CH(CH_3)—COO—(CH_2)_2—OC_2H_5$ |
| Ii.43 | $CH_2—CONH_2$ |
| Ii.44 | $CH_2—CONHCH_3$ |
| Ii.45 | $CH_2—CONHC_2H_5$ |
| Ii.46 | $CH_2—CON(CH_3)_2$ |
| Ii.47 | $CH(CH_3)—CONH_2$ |
| Ii.48 | $CH(CH_3)—CONHCH_3$ |
| Ii.49 | $CH(CH_3)—CONHC_2H_5$ |
| Ii.50 | $CH(CH_3)—CON(CH_3)_2$ |
| Ii.51 | $CH_2—SCH_3$ |
| Ii.52 | $(CH_2)_2—SCH_3$ |
| Ii.53 | $(CH_2)_2—SC_2H_5$ |
| Ii.54 | $(CH_2)_2—SO—CH_3$ |
| Ii.55 | $CH(CH_3)—SO_2—CH_3$ |
| Ii.56 | $(CH_2)_2—SO_2—CH_3$ |
| Ii.57 | $(CH_2)_2$-cyclopropyl |
| Ii.58 | $(CH_2)_2$-cyclopentyl |
| Ii.59 | $(CH_2)_2—O—N{=}C(CH_3)_2$ |
| Ii.60 | $(CH_2)_3—O—N{=}C(CH_3)_2$ |
| Ii.61 | $(CH_2)_2—NO_2$ |
| Ii.62 | $(CH_2)_2—NH_2$ |
| Ii.63 | $(CH_2)_2—NHCH_3$ |

TABLE 2-continued

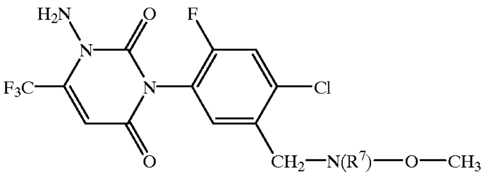

Ii

| No. | $R^7$ |
|---|---|
| Ii.64 | $(CH_2)_2—NH(CH_3)_2$ |
| Ii.65 | $CH_2—OCH_3$ |
| Ii.66 | $CH(CH_3)—OCH_3$ |
| Ii.67 | $CH(CH_3)—OC_2H_5$ |
| Ii.68 | $CH(CH_3)CH_2—OCH_3$ |
| Ii.69 | $(CH_2)_2OH$ |
| Ii.70 | $CH_2—OC_2H_5$ |
| Ii.71 | $CH_2CO—O—$(4-acetoxytetrahydrofuran-3-yl) |
| Ii.72 | $CH_2—OCOCH_3$ |
| Ii.73 | $CH_2—OCOC_2H_5$ |
| Ii.74 | $CH_2—C_6H_5$ |
| Ii.75 | $(CH_2)_2—C_6H_5$ |
| Ii.76 | COOH |
| Ii.77 | $CO—O—CH_3$ |
| Ii.78 | $CO—O—C_2H_5$ |
| Ii.79 | $CO—O$-(n-$C_3H_7$) |
| Ii.80 | $CO—O$-(i-$C_3H_7$) |
| Ii.81 | $CO—O$-(n-$C_4H_9$) |
| Ii.82 | $CO—O$-(i-$C_4H_9$) |
| Ii.83 | $CO—O$-(s-$C_4H_9$) |
| Ii.84 | $CO—O$-(tert-$C_4H_9$) |
| Ii.85 | COO-cyclopropyl |
| Ii.86 | COO-cyclobutyl |
| Ii.87 | COO-cyclopentyl |
| Ii.88 | COO-cyclohexyl |
| Ii.89 | COO-cycloheptyl |
| Ii.90 | COO-cyclooctyl |
| Ii.91 | $COO—CH_2CN$ |
| Ii.92 | $COO—CH_2CH_2CN$ |
| Ii.93 | $COO—CH(CH_3)CN$ |
| Ii.94 | $COO—C(CH_3)_2CN$ |
| Ii.95 | $COO—C(CH_3)_2CH_2CN$ |
| Ii.96 | $COO—CH_2Cl$ |
| Ii.97 | $COO—CH_2CH_2Cl$ |
| Ii.98 | $COO—CH(CH_3)CH_2Cl$ |
| Ii.99 | $COO—CH_2CF_3$ |
| Ii.100 | $COO—CHCl_2$ |
| Ii.101 | $COO—CF_2Cl$ |
| Ii.102 | $COO—CF_3$ |
| Ii.103 | $COO—C_2F_5$ |
| Ii.104 | $COO—CF_2H$ |
| Ii.105 | $COO—CH_2—CH{=}CH_2$ |
| Ii.106 | $COO—CH(CH_3)CH{=}CH_2$ |
| Ii.107 | $COO—CH_2—CH{=}CH—CH_3$ |
| Ii.108 | $COO—CH_2—C{\equiv}CH$ |
| Ii.109 | $COO—CH(CH_3)C{\equiv}CH$ |
| Ii.110 | $COO—C(CH_3)_2C{\equiv}CH$ |
| Ii.111 | $COO—CH_2—COOH$ |
| Ii.112 | $COO—CH_2—CO—OCH_3$ |
| Ii.113 | $COO—CH_2—CO—OC_2H_5$ |
| Ii.114 | $COO—CH_2—CO—O$-(n-$C_3H_7$) |
| Ii.115 | $COO—CH_2—CO—O$-(i-$C_3H_7$) |
| Ii.116 | $COO—CH(CH_3)—CO—OCH_3$ |
| Ii.117 | $COO—CH(CH_3)—CO—OC_2H_5$ |
| Ii.118 | $COO—CH(CH_3)—CO—O$-(n-$C_3H_7$) |
| Ii.119 | $COO—CH(CH_3)—CO—O$-(i-$C_3H_7$) |
| Ii.120 | $COO—CH_2—COO—(CH_2)_2—OCH_3$ |
| Ii.121 | $COO—CH_2—COO—(CH_2)_2—OCH_3$ |
| Ii.122 | $COO—CH(CH_3)—COO—(CH_2)_2—OCH_3$ |
| Ii.123 | $COO—CH(CH_3)—COO—(CH_2)_2—OC_2H_5$ |
| Ii.124 | $COO—CH_2—CONH_2$ |
| Ii.125 | $COO—CH_2—CONHCH_3$ |
| Ii.126 | $COO—CH_2—CONHC_2H_5$ |
| Ii.127 | $COO—CH_2—CON\ (CH_3)_2$ |
| Ii.128 | $COO—CH(CH_3)—CONH_2$ |
| Ii.129 | $COO—CH(CH_3)—CONHCH_3$ |

TABLE 2-continued

Ii

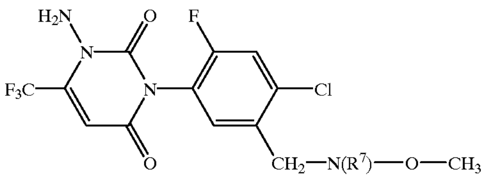

| No. | R$^7$ |
|---|---|
| Ii.130 | COO—CH(CH$_3$)—CONHC$_2$H$_5$ |
| Ii.131 | COO—CH(CH$_3$)—CON(CH$_3$)$_2$ |
| Ii.132 | COO—CH$_2$—SCH$_3$ |
| Ii.133 | COO—(CH$_2$)$_2$—SCH$_3$ |
| Ii.134 | COO—(CH$_2$)$_2$—SC$_2$H$_5$ |
| Ii.135 | COO—(CH$_2$)$_2$—SO—CH$_3$ |
| Ii.136 | COO—(CH$_2$)$_2$—SO$_2$—CH$_3$ |
| Ii.137 | COO—(CH$_2$)$_2$—SO—CH$_3$ |
| Ii.138 | COO—(CH$_2$)$_2$-cyclopropyl |
| Ii.139 | COO—(CH$_2$)$_2$-cyclopentyl |
| Ii.140 | COO—(CH$_2$)$_2$—O—N=C(CH$_3$)$_2$ |
| Ii.141 | COO—(CH$_2$)$_3$—O—N=C(CH$_3$)$_2$ |
| Ii.142 | COO—(CH$_2$)$_2$—NO$_2$ |
| Ii.143 | COO—(CH$_2$)$_2$—NH$_2$ |
| Ii.144 | COO—(CH$_2$)$_2$—NHCH$_3$ |
| Ii.145 | COO—(CH$_2$)$_2$—NH(CH$_3$)$_2$ |
| Ii.146 | COO—CH$_2$—OCH$_3$ |
| Ii.147 | COO—CH(CH$_3$)—OCH$_3$ |
| Ii.148 | COO—CH(CH$_3$)—OC$_2$H$_5$ |
| Ii.149 | COO—CH(CH$_3$)CH$_2$—OCH$_3$ |
| Ii.150 | COO—(CH$_2$)$_2$OH |
| Ii.151 | COO—CH$_2$—OC$_2$H$_5$ |
| Ii.152 | COO—CH$_2$CO—O-( 4-acetoxytetrahydrofuran-3-yl) |
| Ii.153 | COO—CH$_2$—OCOCH$_3$ |
| Ii.154 | COO—CH$_2$—OCOC$_2$H$_5$ |
| Ii.155 | COO—CH$_2$—C$_6$H$_5$ |
| Ii.156 | COO—(CH$_2$)$_2$—C$_6$H$_5$ |
| Ii.157 | COO—CH$_2$-(4-Cl—C$_6$H$_4$) |
| Ii.158 | COO—CH$_2$-(4-CF$_3$—C$_6$H$_4$) |
| Ii.159 | COO—CH$_2$-(3-NO$_2$—C$_6$H$_4$) |
| Ii.160 | CHO |
| Ii.161 | CO—CH$_3$ |
| Ii.162 | CO—C$_2$H$_5$ |
| Ii.163 | CO-(n-C$_3$H$_7$) |
| Ii.164 | CO-(i-C$_3$H$_7$) |
| Ii.165 | CO-(n-C$_4$H$_9$) |
| Ii.166 | CO-(i-C$_4$H$_9$) |
| Ii.167 | CO-(s-C$_4$H$_9$) |
| Ii.168 | CO-(tert-C$_4$H$_9$) |
| Ii.169 | CO-cyclopropyl |
| Ii.170 | CO-cyclobutyl |
| Ii.171 | CO-cyclopentyl |
| Ii.172 | CO-cyclohexyl |
| Ii.173 | CO-cycloheptyl |
| Ii.174 | CO-cyclooctyl |
| Ii.175 | CO—CH$_2$CN |
| Ii.176 | CO—CH$_2$CH$_2$CN |
| Ii.177 | CO—CH(CH$_3$)CN |
| Ii.178 | CO—C(CH$_3$)$_2$CN |
| Ii.179 | CO—C(CH$_3$)$_2$CH$_2$CN |
| Ii.180 | CO—CH$_2$Cl |
| Ii.181 | CO—CH$_2$CH$_2$Cl |
| Ii.182 | CO—CH(CH$_3$)CH$_2$Cl |
| Ii.183 | CO—CH$_2$CF$_3$ |
| Ii.184 | CO—CHCl$_2$ |
| Ii.185 | CO—CF$_2$Cl |
| Ii.186 | CO—CF$_3$ |
| Ii.187 | CO—C$_2$F$_5$ |
| Ii.188 | CO—CF$_2$H |
| Ii.189 | CO—CH$_2$—CH=CH$_2$ |
| Ii.190 | CO—CH(CH$_3$)CH=CH$_2$ |
| Ii.191 | CO—CH$_2$—CH=CH—CH$_3$ |
| Ii.192 | CO—CH$_2$—C≡CH |
| Ii.193 | CO—CH(CH$_3$)C≡CH |
| Ii.194 | CO—C(CH$_3$)$_2$C≡CH |
| Ii.195 | CO—CH$_2$—COOH |

TABLE 2-continued

Ii

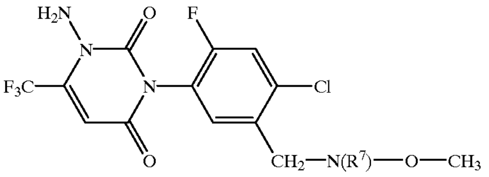

| No. | R$^7$ |
|---|---|
| Ii.196 | CO—CH$_2$—CO—OCH$_3$ |
| Ii.197 | CO—CH$_2$—CO—OC$_2$H$_5$ |
| Ii.198 | CO—CH$_2$—CO—O-(n-C$_3$H$_7$) |
| Ii.199 | CO—CH$_2$—CO—O-(i-C$_3$H$_7$) |
| Ii.200 | CO—CH(CH$_3$)—CO—OCH$_3$ |
| Ii.201 | CO—CH (CH$_3$)—CO—OC$_2$H$_5$ |
| Ii.202 | CO—CH(CH$_3$)—CO—O-(n-C$_3$H$_7$) |
| Ii.203 | CO—CH(CH$_3$)—CO—O-(i-C$_3$H$_7$) |
| Ii.204 | CO—CH$_2$—COO—(CH$_2$)$_2$—OCH$_3$ |
| Ii.205 | COCH$_2$—COO—(CH$_2$)$_2$—OCH$_3$ |
| Ii.206 | CO—CH(CH$_3$)—COO—(CH$_2$)$_2$—OCH$_3$ |
| Ii.207 | CO—CH(CH$_3$)—COO—(CH$_2$)$_2$—OC$_2$H$_5$ |
| Ii.208 | CO—CH$_2$—CONH$_2$ |
| Ii.209 | CO—CH$_2$—CONHCH$_3$ |
| Ii.210 | CO—CH$_2$—CONHC$_2$H$_5$ |
| Ii.211 | CO—CH$_2$—CON(CH$_3$)$_2$ |
| Ii.212 | CO—CH(CH$_3$)—CONH$_2$ |
| Ii.213 | CO—CH(CH$_3$)—CONHCH$_3$ |
| Ii.214 | CO—CH(CH$_3$)—CONHC$_2$H$_5$ |
| Ii.215 | CO—CH(CH$_3$)—CON(CH$_3$)$_2$ |
| Ii.216 | CO—CH$_2$—SCH$_3$ |
| Ii.217 | CO—(CH$_2$)$_2$—SCH$_3$ |
| Ii.218 | CO—(CH$_2$)$_2$—SC$_2$H$_5$ |
| Ii.219 | CO—(CH$_2$)$_2$—SO—CH$_3$ |
| Ii.220 | CO—(CH$_2$)$_2$—SO$_2$—CH$_3$ |
| Ii.221 | CO—(CH$_2$)$_2$—SO—CH$_3$ |
| Ii.222 | CO—(CH$_2$)$_2$-cyclopropyl |
| Ii.223 | CO—(CH$_2$)$_2$-cyclopentyl |
| Ii.224 | CO—(CH$_2$)$_2$—O—N=C(CH$_3$)$_2$ |
| Ii.225 | CO—(CH$_2$)$_3$—O—N=C(CH$_3$)$_2$ |
| Ii.226 | CO—(CH$_2$)$_2$—NO$_2$ |
| Ii.227 | CO—(CH$_2$)$_2$—NH$_2$ |
| Ii.228 | CO—(CH$_2$)$_2$—NHCH$_3$ |
| Ii.229 | CO—(CH$_2$)$_2$—NH(CH$_3$)$_2$ |
| Ii.230 | CO—CH$_2$—OCH$_3$ |
| Ii.231 | CO—CH(CH$_3$)—OCH$_3$ |
| Ii.232 | CO—CH(CH$_3$)—OC$_2$H$_5$ |
| Ii.233 | CO—CH(CH$_3$)CH$_2$—OCH$_3$ |
| Ii.234 | CO—(CH$_2$)$_2$OH |
| Ii.235 | CO—CH$_2$—OC$_2$H$_5$ |
| Ii.236 | CO—CH$_2$CO—O-(4-acetoxytetrahydrofuran-3-yl) |
| Ii.237 | CO—CH$_2$—OCOCH$_3$ |
| Ii.238 | CO—CH$_2$—OCOC$_2$H$_5$ |
| Ii.239 | CO—CH$_2$—C$_6$H$_5$ |
| Ii.240 | CO—(CH$_2$)$_2$—C$_6$H$_5$ |
| Ii.241 | CO—CH$_2$-(4-Cl—C$_6$H$_4$) |
| Ii.242 | CO—CH$_2$-(4-CF$_3$—C$_6$H$_4$) |
| Ii.243 | CO—CH$_2$-(3-NO$_2$—C$_6$H$_4$) |

Very particularly preferred benzylhydroxylamines I are also those which follow:

the compounds Ik.98–Ik.243, which only differ from the corresponding compounds Ii.01–Ii.243 by the fact that R$^1$ is cyano:

Ik

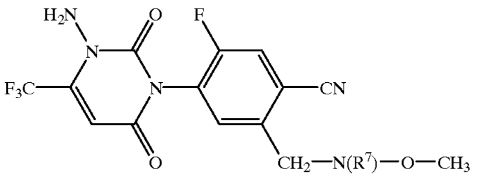

the compounds Il.01–Il.243, which only differ from the corresponding compounds Ii.01–Ii.243 by the fact that $R^2$ is hydrogen:

Il

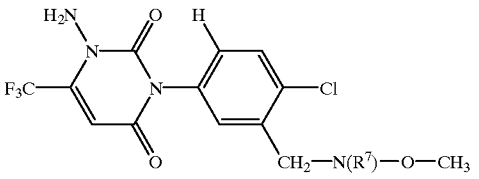

the compounds Im.01–Im.243, which only differ from the corresponding compounds Ii.01–Ii.243 by the fact that $R^1$ is cyano and $R^2$ is hydrogen:

Im

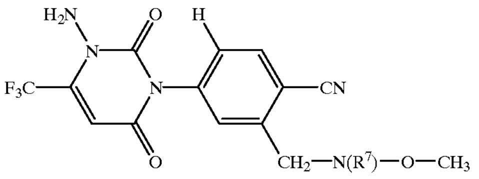

the compounds In.01–In.243, which only differ from the corresponding compounds Ii.01–Ii.243 by the fact that $R^3$ is methyl:

In

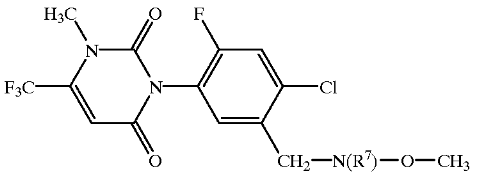

the compounds Io.01–Io.243, which only differ from the corresponding compounds Ii.01–Ii.243 by the fact that $R^1$ is cyano and $R^3$ is methyl:

Io

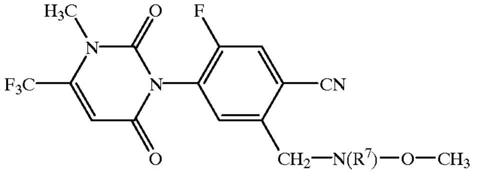

the compounds Ip.01–Ip.243, which only differ from the corresponding compounds Ii.01–Ii.243 by the fact that $R^2$ is hydrogen and $R^3$ is methyl:

Ip

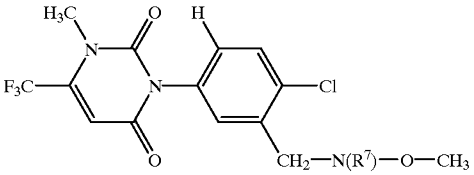

the compounds Iq.01–Iq.243, which only differ from the corresponding compounds Ii.01–Ii.243 by the fact that $R^1$ is cyano, $R^2$ is hydrogen and $R^3$ is methyl:

Iq

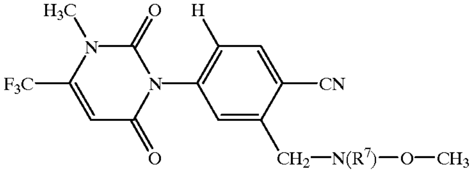

Additionally very particularly preferred compounds Ir (≙ I where Y=oxygen, $R^1$=chlorine, $R^3$=methyl, $R^4$=trifluoromethyl, $R^5$ and $R^6$=hydrogen) are those listed in Table 3 below:

TABLE 3

Ir

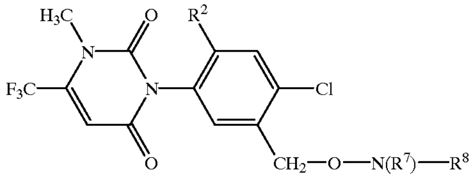

| No. | $R^2$ | $R^7$ | $R^8$ |
|---|---|---|---|
| Ir.01 | F | $CH_3$ | H |
| Ir.02 | F | $C_2H_5$ | H |
| Ir.03 | F | $CH(CH_3)_2$ | H |
| Ir.04 | F | $CH_3$ | $CH_3$ |
| Ir.05 | F | $C_2H_5$ | $CH_3$ |
| Ir.06 | F | $CO—CH_3$ | H |
| Ir.07 | F | $CO—CH_3$ | $CH_3$ |
| Ir.08 | F | $CO—OCH_3$ | H |
| Ir.09 | F | $CO—OCH_3$ | $CH_3$ |
| Ir.10 | F | $CO—OC_2H_5$ | H |
| Ir.11 | F | $CO—OC_2H_5$ | $CH_3$ |
| Ir.12 | F | $CO—CH_2—CO—OC_2H_5$ | H |
| Ir.13 | F | $CO—CH_2—CO—OC_2H_5$ | $CH_3$ |
| Ir.14 | F | $SO_2—CH_3$ | H |
| Ir.15 | F | $SO_2—CH_3$ | $CH_3$ |
| Ir.16 | F | $CH_2—CO—OCH_3$ | H |
| Ir.17 | F | $CH_2—CO—OCH_3$ | $CH_3$ |
| Ir.18 | F | $CH_2—CH{=}C(Cl)—CO—OCH_3$ | H |
| Ir.19 | F | $CH_2—CH{=}C(Cl)—CO—OCH_3$ | $CH_3$ |
| Ir.20 | F | $CO—CH_2—CO—OCH_2—CH{=}CH_2$ | H |
| Ir.21 | F | $CO—CH_2—CO—OCH_2—CH{=}CH_2$ | $CH_3$ |
| Ir.22 | F | $CO—CH_2—CO—NH—CH_3$ | H |
| Ir.23 | F | $CO—CH_2—CO—N(CH_3)—CH_2—CO—OCH_3$ | H |
| Ir.24 | H | $CH_3$ | H |
| Ir.25 | H | $C_2H_5$ | H |
| Ir.26 | H | $CH(CH_3)_2$ | H |
| Ir.27 | H | $CH_3$ | $CH_3$ |
| Ir.28 | H | $C_2H_5$ | $CH_3$ |
| Ir.29 | H | $CO—CH_3$ | H |
| Ir.30 | H | $CO—CH_3$ | $CH_3$ |
| Ir.31 | H | $CO—OCH_3$ | H |

TABLE 3-continued

Ir

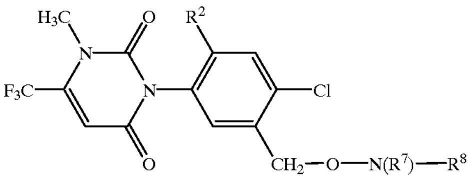

| No. | $R^2$ | $R^7$ | $R^8$ |
|---|---|---|---|
| Ir.32 | H | CO—$OCH_3$ | $CH_3$ |
| Ir.33 | H | CO—$OC_2H_5$ | H |
| Ir.34 | H | CO—$OC_2H_5$ | $CH_3$ |
| Ir.35 | H | CO—$CH_2$—CO—$OC_2H_5$ | H |
| Ir.36 | H | CO—$CH_2$—CO—$OC_2H_5$ | $CH_3$ |
| Ir.37 | H | $SO_2$—$CH_3$ | H |
| Ir.38 | H | $SO_2$—$CH_3$ | $CH_3$ |
| Ir.39 | H | $CH_2$—CO—$OCH_3$ | H |
| Ir.40 | H | $CH_2$—CO—$OCH_3$ | $CH_3$ |
| Ir.41 | H | $CH_2$—CH=C(Cl)—CO—$OCH_3$ | H |
| Ir.42 | H | $CH_2$—CH=C(Cl)—CO—$OCH_3$ | $CH_3$ |
| Ir.43 | H | CO—$CH_2$—CO—$OCH_2$—CH=$CH_2$ | H |
| Ir.44 | H | CO—$CH_2$—CO—$OCH_2$—CH=$CH_2$ | $CH_3$ |
| Ir.45 | H | CO—$CH_2$—CO—NH—$CH_3$ | H |
| Ir.46 | H | CO—$CH_2$—CO—N($CH_3$)—$CH_2$—CO—$OCH_3$ | H |

Finally, very particularly preferred benzylhydroxylamines I are also those which follow:

the compounds Is.01–Is.46, which only differ from the corresponding compounds Ir.01–Ir.46 by the fact that $R^1$ is cyano:

Is

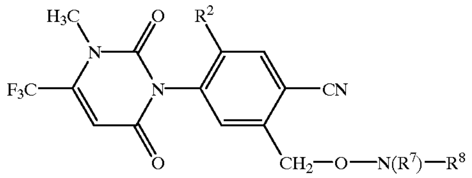

the compounds It.01–It.46, which only differ from the corresponding compounds Ir.01–Ir.46 by the fact that $R^3$ is amino:

It

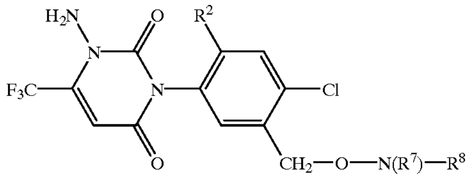

the compounds Iu.01–Iu.46, which only differ from the corresponding compounds Ir.01–Ir.46 by the fact that $R^1$ is cyano and $R^3$ is amino:

Iu

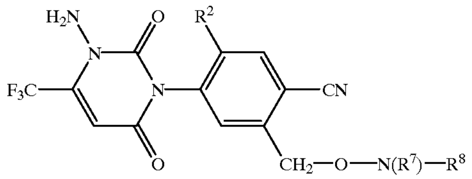

The benzylhydroxylamines of the formula I can be obtained by various routes, for example by one of the following processes:

Process A

Cyclization of an enamine ester of the formula IV or of an enamine carboxylate of the formula V in the presence of a base:

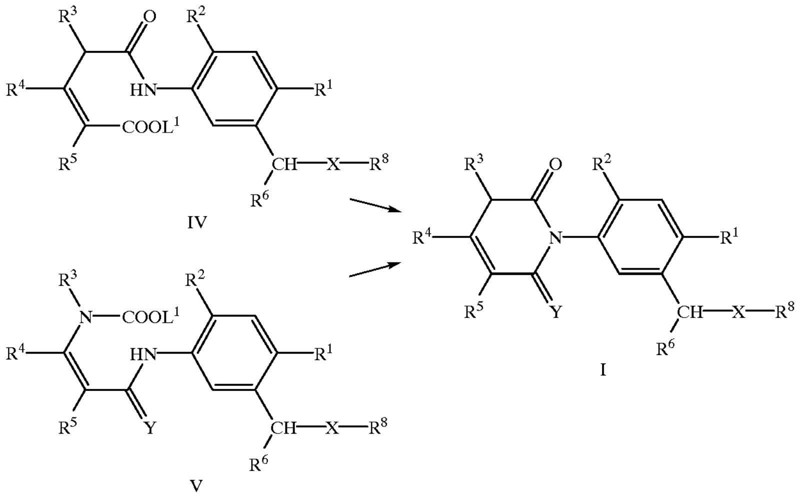

IV

V

I $L^1$ is low-molecular-weight alkyl, preferably $C_1$–$C_4$-alkyl, or phenyl.

As a rule, the cyclization is carried out in an inert organic solvent or diluent which is aprotic, for example in an aliphatic or cyclic ether, such as 1,2-dimethoxyethane, tetrahydrofuran and dioxane, in an aromatic, such as benzene and toluene, or in a polar solvent, such as dimethylformamide and dimethyl sulfoxide. Mixtures of polar solvent and a hydrocarbon, such as n-hexane, are also suitable. Depending on the starting compound, water may also be suitable as the diluent.

Bases which are preferably suitable are alkali metal alcoholates, in particular the sodium alcoholates, alkali metal hydroxides, in particular sodium hydroxide and potassium hydroxide, alkali metal carbonates, in particular sodium carbonate and potassium carbonate, and metal hydrides, in particular sodium hydride. When using sodium hydride as the base, it has proved advantageous to carry out the process in an aliphatic or cyclic ether, in dimethylformamide or in dimethyl sulfoxide.

0.5 to twice the molar amount of base based on the amount of IV or V is usually sufficient for successfully carrying out the reaction.

In general, the reaction temperature is from (−78)° C. to the boiling point of the reaction mixture in question, in particular at from (−60) to 60° C.

If $R^3$ in formula IV or V is hydrogen, the process product is obtained as a metal salt, the metal corresponding to the cation of the base used. The salt can be isolated and purified in a manner known per se or, if desired, converted into the free compound I where $R^3$=hydrogen by means of acid.

Process B

Methylation of a compound I where $R^3$ is hydrogen in the presence of a base:

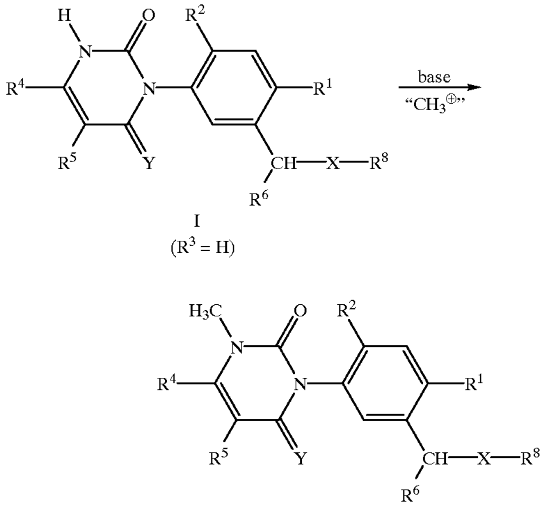

I
($R^3$ = H)

I
($R^3$ = $CH_3$)

Examples of suitable methylating agents are methyl halides, preferably methyl chloride, methyl iodide or methyl bromide, and also dimethyl sulfate, methanesulfonate [sic] (methyl mesylate), methylbenzenesulfonate, methane-p-tolylsulfonate [sic] (methyl tosylate), methane-p-bromobenzenesulfonate [sic] (methyl brosylate), methyl trifluoromethanesulfonate (methyltriflate) and diazomethane.

As a rule, the process is carried out in an inert organic solvent, for example in a protic solvent, such as the lower alcohols, preferably in ethanol, if desired as a mixture with water, or in an aprotic solvent, e.g. in an aliphatic or cyclic ether, preferably in 1,2-dimethoxyethane, tetrahydrofuran or dioxane, in an aliphatic ketone, preferably in acetone, in an amide, preferably in dimethylformamide, in a sulfoxide, preferably in dimethyl sulfoxide, in a urea, such as tetramethylurea, and 1,3-dimethyltetrahydro2(1H)-pyrimidinone [sic], in a carboxylic ester, such as ethyl acetate, or in a halogenated aliphatic or aromatic hydrocarbon, such as dichloromethane and chlorobenzene.

Suitable bases are inorganic bases, e.g. carbonates, such as sodium carbonate and potassium carbonate, hydrogen carbonates, such as sodium hydrogen carbonate and potassium hydrogen carbonate, or alkali metal hydrides, such as sodium hydride and potassium hydride, and organic bases, e.g. amines, such as triethylamine, pyridine and N,N-diethylaniline, or alkali metal alcoholates, such as sodium methanolate, sodium ethanolate and potassium tert-butanolate.

The amount of base and methylating agent is preferably in each case 0.5 times to twice the molar amount based on the amount of starting compound.

In general, the reaction temperature is from 0° C. up to the boiling point of the reaction mixture, in particular at from 0 to 60° C.

A preferred process variant consists in methylating the salt of I, which has been obtained by cyclizing IV ($R^3$=H) or V ($R^3$=H) in accordance with process A), without isolation from the reaction mixture which can still comprise excess base, e.g. sodium hydride, sodium alcoholate or sodium carbonate.

Unless they can be prepared directly by the cyclization described as method A) under alkaline conditions, the salts of those compounds I where $R^3$ is hydrogen can also be obtained in a manner known per se from the process products of method A). To this end, for example the aqueous solution of an inorganic or organic base is treated with the benzylhydroxylamine I where $R^3$ is hydrogen. The salt is generally formed sufficiently rapidly at as little as 20–25° C.

It is particularly advantageous to prepare the sodium salt by dissolving the benzylhydroxylamine I ($R^3$=hydrogen) in aqueous sodium hydroxide solution at 20–25° C., approximately equivalent amounts of benzylhydroxylamine and sodium hydroxide being employed. The salt of the benzylhydroxylamine can then be isolated for example by precipitation with a suitable inert solvent or by evaporation of the solvent.

Salts of the benzylhydroxylamines I ($R^3$=H) whose metal ion is not an alkali metal ion can generally be prepared by double decomposition of the corresponding alkali metal salt in aqueous solution. Compounds which can be prepared in this manner are, for example, benzylhydroxylamine metal salts which are insoluble in water.

Process C

Reaction of a benzylhydroxylamine of the formula I where $R^3$ is hydrogen with an electrophilic aminating reagent in the presence of a base:

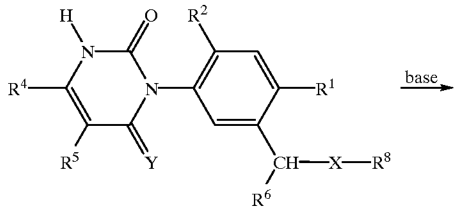

I
($R^3$ = H)

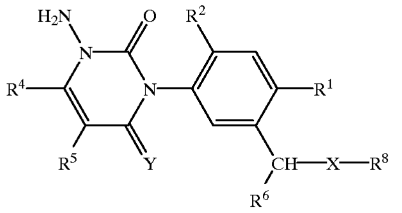

I
($R^3$ = $CH_3$)

An aminating reagent which has proved particularly useful to date is 2,4-dinitrophenoxyamine, but hydroxylamine-O-sulfonic acid (HOSA), which has already been disclosed in the literature as an aminating reagent (cf., for example, E. Hofer et al., Synthesis 1983, 466; W. Friedrichsen et al., Heterocycles 20 (1983) 1271; H. Hart et al., Tetrahedron Lett. 25 (1984) 2073; B. Vercek et al., Monatsh. Chem. 114 (1983) 789; G. Sosnousky et al., Z. Naturforsch. 38 (1983) 884; R. S. Atkinson et al., J. Chem. Soc. Perkin Trans. 1987, 2787), can, for example, also be used.

The amination can be carried out in a manner known per se (see, for example, T. Sheradsky, Tetrahedron Lett. 1968, 1909; M. P. Wentland et al., J. Med. Chem. 27 (1984) 1103 and, in particular, EP-A 240 194, EP-A 476 697, EP-A 517 181 and WO 95/06641, which teach the amination of uracils).

The reaction is normally carried out in a polar solvent, e.g. in dimethylformamide, N-methylpyrrolidone, dimethyl sulfoxide, or in ethyl acetate, which has proved as particularly suitable to date.

Examples of suitable bases are alkali metal carbonates, such as potassium carbonate, alkali metal alcoholates, such as sodium methylate and potassium tert-butanolate, or alkali metal hydrides, such as sodium hydride.

The amount of base and aminating agent is preferably in each case 0.5 times to twice the molar amount, based on the amount of starting compound.

Depending on the meanings of $R^7$ and $R^8$, it may be necessary to protect these substituents against amination in a manner known per se. This is particularly to be recommended if $R^7$ or $R^8$ is hydrogen.

Process D

Sulfuration of a benzylhydroxylamine of the formula I where Y=oxygen:

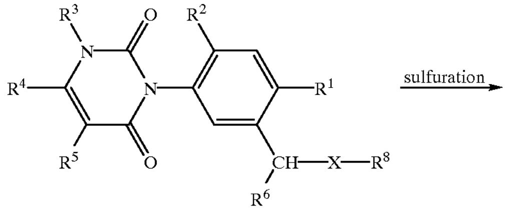

I
(Y = O)

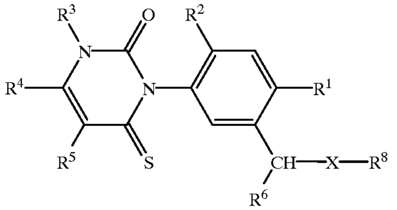

I
(Y = S)

The sulfuration is generally carried out in an inert solvent or diluent, for example in an aromatic hydrocarbon such as toluene and the xylenes, in an ether, such as diethyl ether, 1,2-dimethoxyethane and tetrahydrofuran, or in an organic amine, such as pyridine.

Particularly suitable as sulfurating reagents are phosphorus(V) sulfide and 2,4-bis(4-methoxyphenyl)-1,3,2,4-dithiadiphosphetane-2,4-dithione ("Lawesson reagent").

In general, 1 to 5 times the molar amount based on the starting compound to be sulfurated is sufficient for an essentially complete reaction.

The reaction temperature is normally at from 20 to 200° C., preferably at from 40° C. to the boiling point of the reaction mixture.

Process E

Alkylation or acylation of a benzylhydroxylamine of the formula I where $R^7$ is hydrogen in the presence of a base:

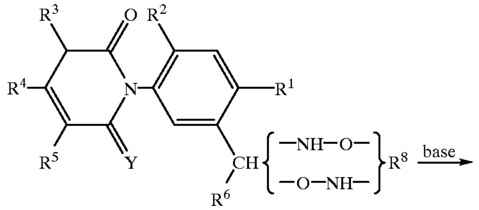

I
($R^7$ = H)

I
($R^7 \neq$ H)

The alkylation can be carried out for example with the halide, preferably the chloride or bromide, the sulfate, sulfonate, preferably the methanesulfonate (mesylate), benzenesulfonate, p-toluenesulfonate (tosylate), p-bromobenzenesulfonate (brosylate), the trifluoromethanesulfonate (triflat) or the diazo compound of an unsubstituted or substituted alkane, cycloalkane, haloalkane, alkene or alkyne.

Suitable acylating agents are, e.g., the acid halides, in particular the acid chlorides, the anhydrides, isocyanates and sulfonyl chlorides of substituted or unsubstituted alkane-, cycloalkane-, alkene-, alkyne- or phenylcarboxylic acids. Alternatively, the free acids or their anhydrides are suitable if the process is then carried out in the presence of a condensing agent, such as carbonyl diimidazole and dicyclohexylcarbodiimide.

The process is usually carried out in an inert organic solvent, preferably in an aprotic solvent, e.g. an aliphatic or cyclic ether, such as 1,2-dimethoxyethane, tetrahydrofuran and dioxane, an aliphatic ketone, such as acetone, an amide, such as dimethylformamide, a sulfoxide, such as dimethyl sulfoxide, a urea, such as tetramethylurea and 1,3-dimethyltetrahydro-2(1H)-pyrimidinone, a carboxylic ester, such as ethyl acetate, or a halogenated aliphatic or aromatic hydrocarbon, such as dichloromethane, and chlorobenzene.

Suitable bases are inorganic bases, e.g. alkali metal carbonates, such as sodium carbonate and potassium carbonate, alkali metal hydrogen carbonates, such as sodium hydrogen carbonate and potassium hydrogen carbonate, or alkali metal hydrides, such as sodium hydride and potassium hydride, but also organic bases, e.g. amines, such as triethylamine, pyridine and N,N-diethylaniline, or alkali metal alcoholates, such as sodium methanolate, sodium ethanolate and potassium tert-butanolate.

The amount of base and alkylating agent is preferably 0.5 times to twice the molar amount based on the amount of I where $R^7$=hydrogen.

In general, a reaction temperature of from 0° C. to the boiling point of the reaction mixture, in particular from 0 to 60° C., is recommended.

Problems in connection with regioselectivity which may occur in the case of starting compounds where $R^3$=hydrogen can be avoided in a manner known per se (use of 2 equivalents of base, introduction of a protective group, and the like).

Process F

Reduction of an oximino compound of the formula VII:

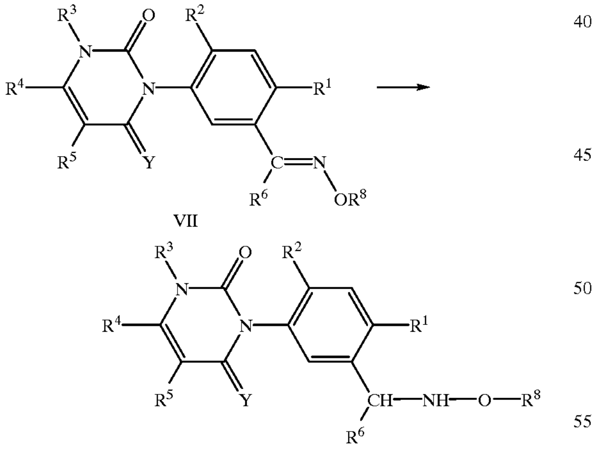

VII

I ($R^7$ = H)

Examples of suitable reducing agents are hydrides, such as borane complexes, e.g. borane-dimethyl sulfide or borane-pyridine complexes, moreover silanes, such as triethylsilane and diphenylmethylsilane, or molecular hydrogen using a catalyst, such as platinum-on-charcoal.

If hydrogen is used, it is recommended to carry out the reaction under acidic conditions, e.g. in an organic or inorganic acid as the solvent.

The hydrogen pressure is generally at from atmospheric pressure to a superatmospheric pressure of approximately 10 bar.

In general, the reduction is successfully carried out at from (−5) to +50° C.

The amount of reducing agent is not critical. The process can be carried out with a smaller amount of reducing agent based on the amount of VII or else with an excess, approximately up to 15 times the molar amount. 0.5 times to twice the molar amount of reducing agent based on the oximino compound VII is preferably used.

Process G

Cleavage of an alkylideneaminoxy compound of the formula VIII:

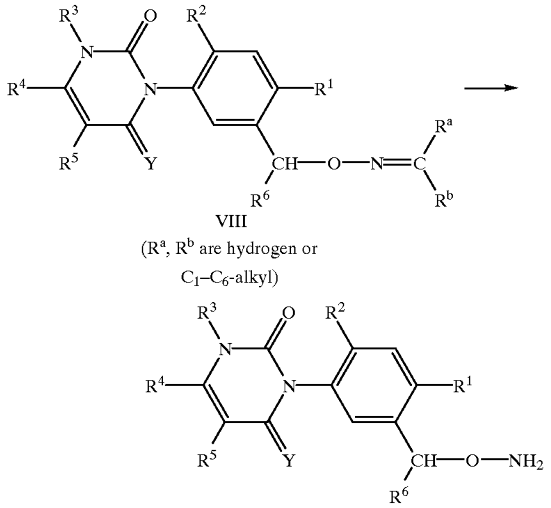

VIII ($R^a$, $R^b$ are hydrogen or $C_1$–$C_6$-alkyl)

I ($R^7$, $R^8$ = H)

The cleavage is expediently carried out using a Brønsted acid as catalyst. Normally, 0.5–2 times the molar amount of acid based on the amount of VIII will suffice. Suitable examples of acids are organic acids such as acetic acid and inorganic acids such as sulfuric acid and hydrochloric acid.

The reaction can be carried out directly in the acid or in an inert solvent, eg. in toluene.

The cleavage is advantageously carried out in the presence of an oxime such as hydroxylamine and methylhydroxylamine, in which case the oxime is employed in approximately equimolar amounts or in an excess of up to 20 times the molar amount based on the amount of VIII. In general, a reaction temperature of from 0° C. to the boiling point of the reaction mixture is recommended.

The alkylideneaminoxy compounds VIII can be obtained, in turn, for example from benzyl derivatives IX:

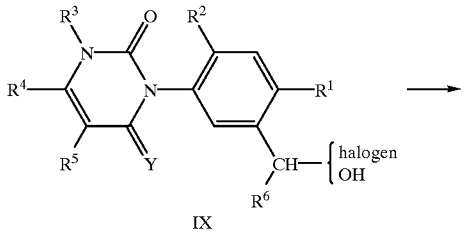

IX

-continued

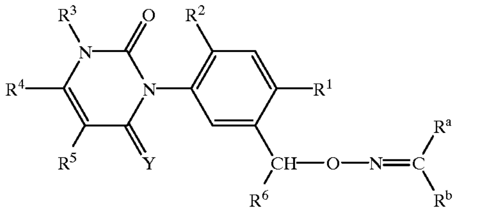

VIII

As a rule, the reaction is carried out in an inert solvent/diluent with the desired alkylideneaminohydroxide HO—N=C($R^a$,$R^b$). If IX is employed as the benzyl halide (IXa), it is expedient to carry out the process in the presence of an organic base such as triethylamine or of an inorganic base such as sodium carbonate and potassium carbonate. If, in contrast, a benzyl alcohol (IXb) is used as starting material, a condensing auxiliary such as carbodiimidazole is required.

Examples of suitable solvents are aromatics such as toluene and xylenes, esters such as ethyl acetate, ethers such as diethyl ether and tetrahydrofuran, halogenated aliphatics such as methylene chloride or basic solvents such as pyridine and dimethylformamide.

IX and alkylideneaminohydroxide are expediently employed in approximately stoichiometric amounts, or else the process is carried out using a slight excess of one or the other reactant of up to approximately 10 mol %.

In general, the reaction is carried out at from 0° C. to the boiling point of the reaction mixture.

Process H

Reaction of benzyl alcohols IXa with hydroxylamines HO—N($R^7$)—$R^8$:

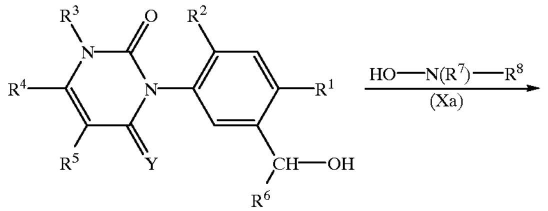

IXa

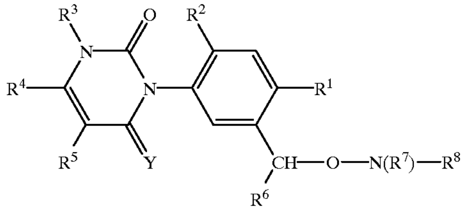

I

The process is preferably carried out in the presence of a condensing auxiliary such as carbodiimidazole in amounts of, normally, 0.5 to 2 times the molar amount based on the amount of IXa.

As a rule, the reaction is carried out in an inert organic solvent, eg. a hydrocarbon such as toluene and the xylenes, an ester such as ethyl acetate or an ether such as diethyl ether and tetrahydrofuran.

IX and Xa are expediently employed in approximately stoichiometric amounts, or else a slight excess of one or the other reactant of up to approximately 10 mol % is used.

In general, a reaction temperature of from 0° C. to the boiling point of the reaction mixture is recommended.

Process K

Halogenation of a benzylhydroxylamine of the formula I where $R^5$ is hydrogen:

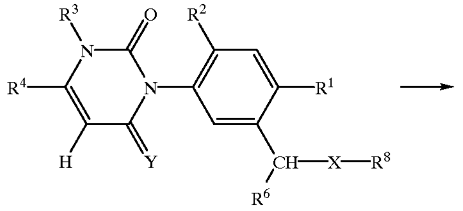

I
($R^5$ = H)

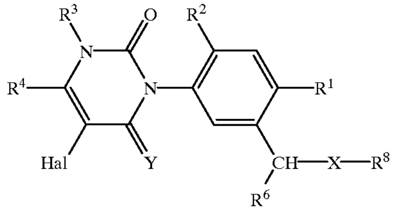

I
($R^5$ = halogen)

The halogenation is generally carried out in an inert organic solvent or diluent. Suitable agents for the chlorination and bromination are, for example, aliphatic carboxylic acids, such as acetic acid, or chlorinated aliphatic hydrocarbons such as methylene chloride, chloroform and carbon tetrachloride.

Particularly preferred for the iodination are low-boiling aliphatic carboxylic acids, such as acetic acid.

Particularly suitable agents for the chlorination and bromination are elemental chlorine or bromine, or else sulfuryl chloride or sulfuryl bromide, at a reaction temperature of, preferably, from 0 to 60° C., in particular from 10 to 30° C.

If desired, the chlorination and bromination can be carried out in the presence of an acid-binding agent, particularly preferred agents being sodium acetate and tertiary amines such as triethylamine, dimethylaniline and pyridine.

Particularly preferred as iodinating agent is elemental iodine, the reaction temperature in this case being from approximately 0 to 110° C., preferably at from 10 to 30° C.

The iodination proceeds particularly advantageously in the presence of a mineral acid, such as fuming nitric acid.

The amount of halogenating agent is not critical; usually, equimolar amounts of halogenating agent or an excess of up to approximately 200 mol % based on the starting compound (I where $R^5$=hydrogen) are used.

Excess iodine can be removed for example, after the reaction by means of saturated aqueous sodium hydrogen sulfite solution.

Process L

Alkylation of a hydroxylamine or of a hydroxamic acid with a benzyl halide or benzyl alcohol derivative of the formula XI in the presence of a base:

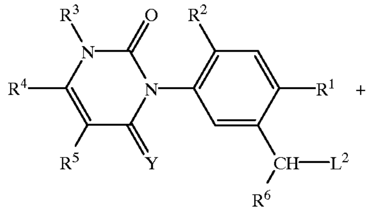

XI $HN(R^7)—O—R^8$
(Xb)
or
$HO—N(R^7)—R^8$
($Xa; R^7, R^8 \neq H$)

I $L^2$ is halogen or lower-alkylsulfonate, lower-haloalkylsulfonate or phenylsulfonate, which may be substituted.

As a rule, the process is carried out in an inert organic solvent, suitable solvents being, in particular, aprotic solvents, e.g. aliphatic or cyclic ethers, such as, preferably, 1,2-dimethoxyethane, tetrahydrofuran and dioxane, aliphatic ketones, such as, preferably, acetone, amides such as, preferably, dimethylformamide, sulfoxides such as, preferably, dimethyl sulfoxide, ureas such as tetramethylurea and 1,3-dimethyltetrahydro-2(1H)-pyrimidinone, carboxylic esters such as ethyl acetate, or halogenated aliphatic or aromatic hydrocarbons, such as dichloromethane and chlorobenzene.

Suitable bases are inorganic bases, e.g. carbonates, such as the alkali metal carbonates, in particular sodium carbonate and potassium carbonate, hydrogen carbonates, such as the alkali metal hydrogen carbonates, in particular sodium hydrogen carbonate and potassium hydrogen carbonate, or alkali metal hydride, such as sodium hydride and potassium hydride, but also organic bases, e.g. amines, such as triethylamine, pyridine and N,N-diethylaniline, or alkali metal alcoholates, such as sodium methanolate, sodium ethanolate and potassium tert-butanolate.

The amounts of base and alkylating agent XI are normally in each case 0.5 times to twice the molar amount based on the amount of X.

In general, the reaction is carried out at from (−78)° C. to the boiling point of the reaction mixture, in particular at from (−60) to 60° C.

The enamine esters of the formula IV are novel. They can be prepared by methods known per se, for example by one of the following processes:

M

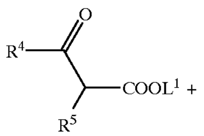

XII

-continued

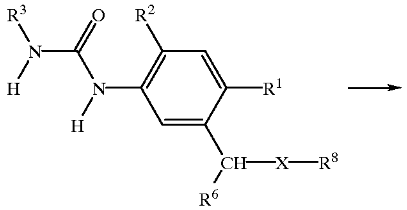

XIII

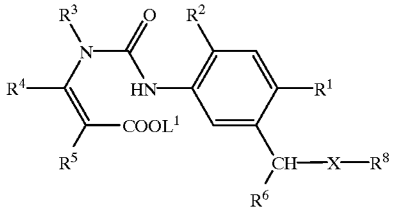

IV

The process is preferably carried out under essentially anhydrous conditions in an inert solvent or diluent, particularly preferably in the presence of an acidic or alkaline catalyst.

Suitable solvents or diluents are, in particular, organic solvents which form an azeotropic mixture with water, for example aromatics such as benzene, toluene and xylenes, halogenated hydrocarbons, such as methylene chloride, chloroform, carbon tetrachloride and chlorobenzene, aliphatic and cyclic ethers, such as 1,2-dimethoxyethane, tetrahydrofuran and dioxane, or cyclohexane, but also alcohols, such as methanol and ethanol.

Acidic catalysts which are preferably suitable are strong mineral acids such as sulfuric acid and hydrochloric acid, phosphorus-containing acids, such as orthophosphoric acid and polyphosphoric acid, organic acids such as p-toluenesulfonic acid, and acidic cation exchangers such as “Amberlyst 15” (by Fluka).

Suitable basic catalysts are, e.g., metal hydrides, such as sodium hydride, and, particularly preferably, metal alcoholates, such as sodium methanolate and ethanolate.

XIII and the β-ketoester XII are expediently employed in approximately stoichiometric amounts, or else the process is carried out with a slight excess of one or the other component, up to approximately 10 mol %.

0.5 times to twice the molar amount of catalyst based on the amount of one of the starting compounds is usually sufficient.

In general, the reaction is carried out at from 60 to 120° C., preferably at the boiling point of the reaction mixture to rapidly remove the water which forms.

N

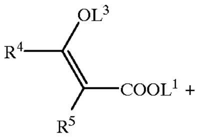

XIV

-continued

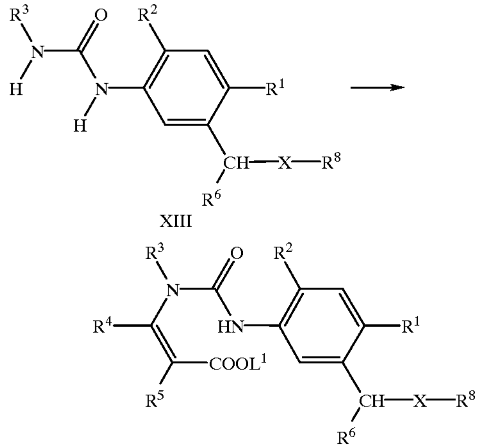

XIII

IV $L^3$ is $C_1$–$C_4$-alkyl or phenyl.

This reaction can be carried out for example in an inert organic solvent which is miscible with water, for example in an aliphatic or cyclic ether, such as 1,2-dimethoxyethane, tetrahydrofuran and dioxane, or a lower alcohol, in particular ethanol, the reaction temperature usually being at from 50 to 100° C., preferably at the boiling point of the reaction mixture.

However, the reaction can also be carried out in an aromatic diluent such as benzene, toluene and xylenes, in which case an addition of either an acidic catalyst, such as hydrochloric acid and p-toluenesulfonic acid, or of a base, e.g. an alkali metal alcoholate, such as sodium methanolate and sodium ethanolate, is advisable. In this process variant, again, the reaction temperature is usually at from 50 to 100° C., but preferably at from 60 to 80° C. As regards the quantities, the information given for method M) also applies here.

O

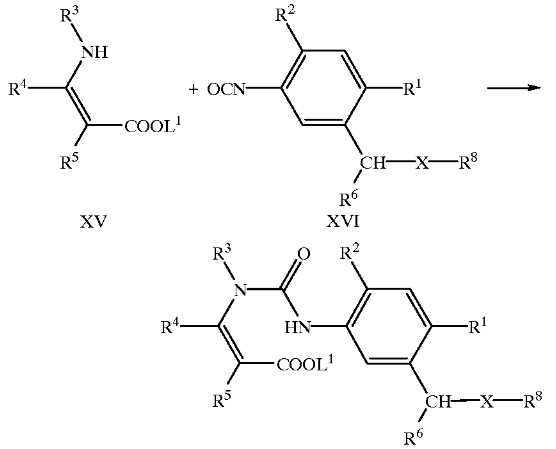

XV XVI

IV

The reaction is expediently carried out in the presence of an essentially anhydrous aprotic organic solvent or diluent, for example an aliphatic or cyclic ether, such as diethyl ether, 1,2-dimethoxyethane, tetrahydrofuran and dioxane, an aliphatic or aromatic hydrocarbon, such as n-hexane, benzene, toluene and xylene, a halogenated, aliphatic hydrocarbon, such as methylene chloride, chloroform, carbon tetrachloride, 1,2-dichloroethane and chlorobenzene, an aprotic, polar solvent, such as dimethylformamide, hexamethylphosphoric triamide and dimethyl sulfoxide, or a mixture of these.

If desired, the process can also be carried out in the presence of a metal hydride base, such as sodium hydride and potassium hydride, an alkali metal alcoholate or alkaline earth metal alcoholate, such as sodium methanolate, sodium ethanolate and potassium tert-butanolate, or an organic tertiary base, such as triethylamine and pyridine, it being possible for the organic base to act simultaneously as the solvent.

It is expedient to employ the starting compounds in stoichiometric amounts, or else to use a small excess of one or the other component of up to approximately 10 mol %. If the process is carried out without solvent in the presence of an organic base, it is recommended to employ a substantial excess of the latter.

A reaction temperature of from (−80) to 50° C., in particular (−60) to 30° C., is usually sufficient.

In a particularly preferred embodiment, the resulting enamine ester IV is converted directly (i.e. "in situ") into the corresponding desired product I in accordance with process A) using an excess of base. Any by-products (e.g. C-alkylation products in the case of compounds where $R^5$=hydrogen) can be removed by means of conventional separation processes, such as crystallization and chromatography.

P

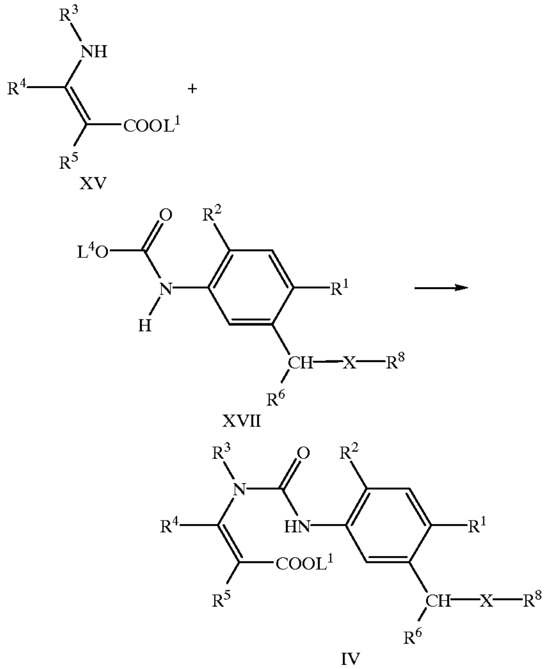

XV

XVII

IV $L^4$ is $C_1$–$C_4$-alkyl or phenyl.

This reaction is expediently carried out in an aprotic, polar solvent or diluent, such as dimethylformamide, 2-butanone, dimethyl sulfoxide and acetonitrile, advantageously in the presence of a base, for example an alkali metal alcoholate or alkaline earth metal alcoholate, in particular a sodium alkanolate, such as sodium methanolate, an alkali metal carbonate or alkaline earth metal carbonate, in particular sodium carbonate, or an alkali metal hydride, such as lithium hydride and sodium hydride. 0.5 times to twice the molar amount of base, based on the amount of XV or XVII, is usually sufficient.

The reaction temperature is generally at from 80 to 180° C., preferably at the boiling point of the reaction mixture.

With regard to the ratios of the starting compounds, the information given for method M) applies.

In a particularly preferred embodiment, a sodium alcoholate is used as the base, and the alcohol which is formed in the course of the reaction is distilled off continuously. The enamine esters IV which are prepared in this manner can be cyclized from the reaction mixture without isolation in accordance with process A) to give a salt of the corresponding benzylhydroxylamine I.

Q

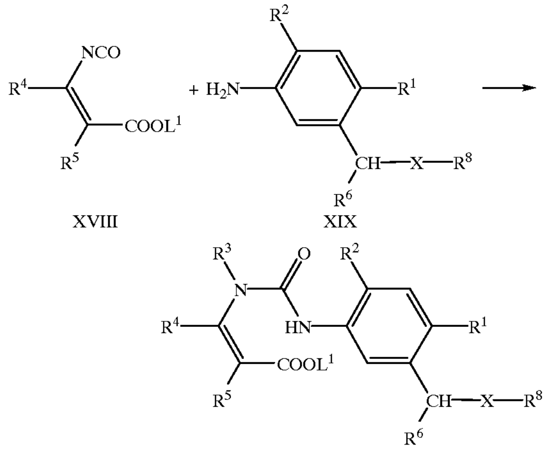

XVIII XIX

IV

This reaction is expediently carried out in an essentially anhydrous aprotic organic solvent or diluent, for example in the presence of an aliphatic or cyclic ether, such as diethyl ether, 1,2-dimethoxyethane, tetrahydrofuran and dioxane, an aliphatic or aromatic hydrocarbon, such as n-hexane, benzene, toluene and the xylenes, a halogenated, aliphatic hydrocarbon, such as methylene chloride, chloroform, carbon tetrachloride, 1,2-dichloroethane and chlorobenzene, an aprotic, polar solvent, such as dimethylformamide, hexamethylphosphoric triamide and dimethyl sulfoxide, or a mixture of these.

If desired, the process can also be carried out in the presence of a metal hydride base, such as sodium hydride and potassium hydride, an alkali metal alcoholate or alkaline earth metal alcoholate, such as sodium methanolate, sodium ethanolate and potassium tert-butanolate, or an organic nitrogen base, such as triethylamine and pyridine, it being possible for the organic base to act simultaneously as the solvent.

It is expedient to employ the starting compounds in stoichiometric amounts or to use one of the components in an excess of up to approximately 20 mol %. If the process is carried out without solvent in the presence of an organic base, it is advantageous to use the latter in an even larger excess.

The reaction temperature is generally at from (−80) to 150° C., preferably at from (−30)° C. to the boiling point of the reaction mixture in question.

The enamine carboxylates of the formula V are also novel; they too can be prepared in a manner known per se, for example from an aniline derivative of the formula XV in accordance with the following reaction scheme R):

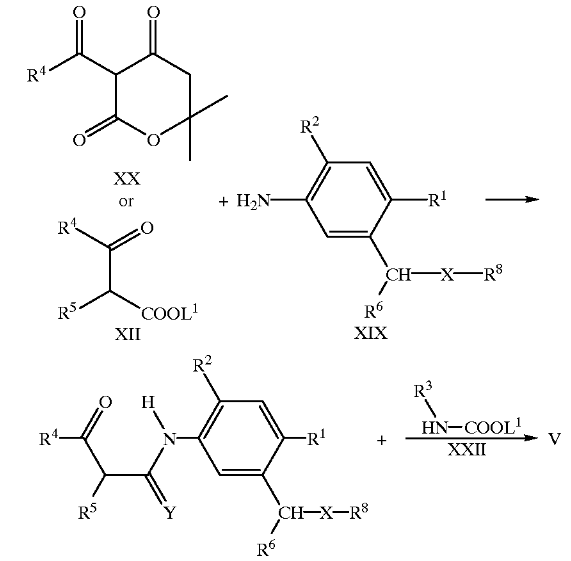

XX or XII XIX

XXII

XXI

The reaction of XX with XIX is preferably carried out in an anhydrous inert aprotic solvent, for example in a halogenated hydrocarbon, such as methylene chloride, chloroform, carbon tetrachloride and chlorobenzene, an aromatic hydrocarbon, such as benzene, toluene and the xylenes, or an aliphatic or cyclic ether, such as diethyl ether, dibutyl ether, 1,2-dimethoxyethane, tetrahydrofuran and dioxane.

The reaction temperature for this reaction (of XX with XIX) is generally at from approximately 70 to 140° C., in particular 100 to 120° C.

The reaction of XII with XIX is an aminolysis, which is generally carried out either in the absence of a solvent [cf., for example, J. Soc. Dyes Col. 42, 81 (1926), Ber. 64, 970 (1931); Org. Synth., Coll. Vol. IV, 80 (1963) and J. Am. Chem. Soc. 70, 2402 (1948)] or in an inert anhydrous solvent/diluent, in particular in an aprotic solvent, for example in an aromatic, such as toluene and the xylenes, or a halogenated aromatic, such as chlorobenzene.

It is recommended to carry out the process in the presence of an alkaline catalyst, for example a higher-boiling amine [see, for example, Helv. Chim. Acta 11, 779 (1928) and U.S. Pat. No. 2,416,738] or pyridine.

The reaction temperature is preferably at from approximately 20 to 160° C.

The starting compounds are in each case expediently employed in approximately stoichiometric amounts, or else the process is carried out with a small excess of one or the other component of up to approximately 10 mol %. If the process is carried out in the presence of an alkaline catalyst, 0.5 times to twice the molar amount of catalyst based on the amount of one of the educts is generally sufficient.

The subsequent reaction of the resulting compounds of the formula XXI with the amine $HN(R^3)—COOL^1$ is advantageously carried out in an essentially anhydrous solvent/diluent under atmospheric pressure, particularly preferably in the presence of an acidic catalyst.

To prepare enamine carboxylates V where $R^3$=amino, it is recommended to employ compounds XXII with a protected amino group (e.g. as a hydrazone).

Suitable solvents/diluents are, in particular, organic liquids which can be mixed with water to give an azeotropic mixture, for example aromatics, such as benzene, toluene and the xylenes, or halogenated hydrocarbons, such as carbon tetrachloride and chlorobenzene.

Suitable catalysts are, in particular, strong mineral acids, such as sulfuric acid, organic acids, such as p-toluenesulfonic acid, phorphorus-containing acids, such as orthophosphoric acid and polyphosphoric acid, or acidic cation exchangers, such as "Amberlyst 15" (by Fluka).

The reaction temperature is generally at from approximately 70 to 150° C.; however, to rapidly remove the resulting reaction water, the process is expediently carried out at the boiling point of the reaction mixture in question.

The compounds of the formulae XIII, XVI, XVII and XXI are also novel. They too can be prepared in a manner known per se, particularly advantageously from the compounds of the formula XIX:

S): "Phosgenation" of Compounds of the formula XIX and hydrolysis of the process products XVI using ammonia (derivatives):

$$XIX \xrightarrow[ClCO-OCCl_3]{COCl_2} XVI \longrightarrow XIII$$

The process can be carried out in an inert essentially anhydrous solvent/diluent or in the absence of a solvent. The amino group is preferably converted into the isocyanate group by means of phosgene or trichloromethyl chloroformate.

Suitable solvents/diluents are, in particular, aprotic organic solvents, for example aromatics, such as toluene and the xylenes, halogenated hydrocarbons, such as methylene chloride, chloroform, 1,2-dichloroethane and chlorobenzene, aliphatic or cyclic ethers, such as 1,2-dimethoxyethane, tetrahydrofuran and dioxane, esters, such as ethyl acetate, and mixtures of these.

Depending on the aniline derivative XIX employed, it may be advantageous to add a base such as triethylamine, for example in 0.5 to twice the molar amount based on the amount of XIX.

The phenyl isocyanates XVI are usually formed at from 50° C. to the boiling point of the reaction mixture; they can subsequently be reacted with ammonia or with a reactive ammonia derivative to give the phenylurea derivatives XIII.

T): Reaction with alkali metal cyanates:

$$XIX \xrightarrow{M^+\ OCN^-} XIII$$

$M^+$ is the equivalent of a metal ion, in particular an alkali metal ion, such as sodium and potassium.

The reaction is generally carried out in an inert solvent/diluent, for example in an aromatic hydrocarbon, such as toluene and the xylenes, in an aliphatic or cyclic ether, such as tetrahydrofuran and dioxane, in a lower alcohol, such as methanol and ethanol, in water, or in a mixture of these.

The amount of cyanate is not critical; however, at least equivalent amounts of aniline compound XIX and cyanate are required for a complete reaction; however, an excess of cyanate of up to approximately 100 mol % may also be advantageous.

The reaction temperature is generally at from 0° C. to the boiling point of the reaction mixture.

U): Reactions with esters $L^4O—CO—L^5$

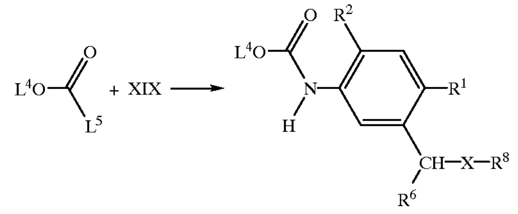

$L^5$ is halogen, preferably chlorine or bromine, $C_1$–$C_4$-alkoxy or phenoxy.

Suitable solvents/diluents are, for example, aromatic hydrocarbons, such as toluene and the xylenes, halogenated hydrocarbons, such as methylene chloride, chloroform, 1,2-dichloroethane and chlorobenzene, aliphatic or cyclic ethers, such as 1,2-dimethoxyethane, tetrahydrofuran and dioxane, esters, such as ethyl acetate, alcohols, such as methanol and ethanol, or water. Mixtures of an organic solvent and water are also suitable.

The process is preferably carried out in the presence of a base, e.g. in the presence of an alkali metal hydroxide, alkali metal carbonate or alkali metal alcoholate, such as sodium hydroxide, sodium carbonate, sodium methanolate and sodium ethanolate, or of a tertiary amine, such as pyridine and triethylamine.

If desired, a catalyst, e.g. a Lewis acid, such as antimony trichloride, may also be added.

The starting compounds and the base are expediently employed in approximately stoichiometric amounts, but one or the other component may also be present in an excess of up to approximately 100 mol %.

The amount of catalyst is generally 1 to 50 mol %, preferably 2 to 30 mol %, based on the amount of aniline compound XIX employed.

The reaction is usually successfully carried out at from (−40)° C. to the boiling point of the reaction mixture.

The aniline compounds of the formula XIX are also novel. They are usually synthesized from the corresponding nitro compounds XXIII by means of hydrogenation or from anilines of the formula XXIV, which can be converted into the corresponding aniline compounds of the formula XIX in accordance with process F):

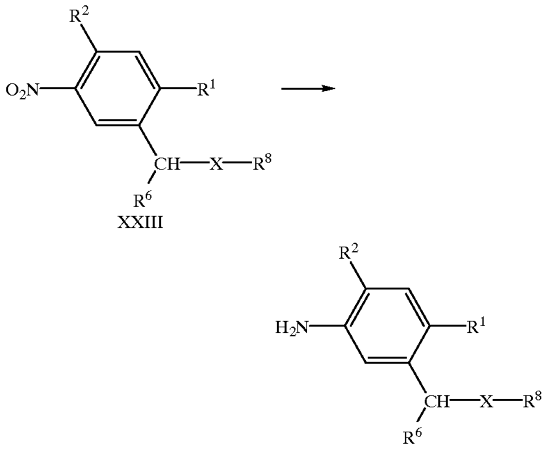

XXIII

XIX

-continued

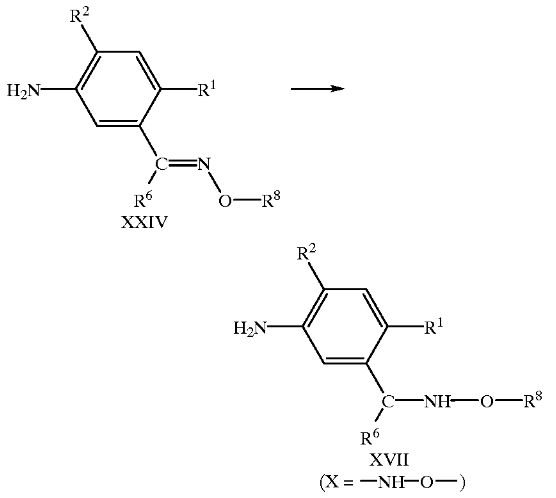

The nitro compounds of the formula XXIII, too, are novel. They can be synthesized by processes known per se, for example by nitration of the corresponding benzylamines.

The compounds of the formula VII, X, XI, XII, XIV, XV, XVIII, XIX and XXIV are known or can be synthesized in a manner known per se (cf., for example, WO 92/02088 and DE-A 42 37 920).

Unless otherwise indicated, all processes described above are expediently carried out under atmospheric pressure or under the inherent pressure of the reaction mixture in question.

Depending on the substitution pattern of the target compounds, it may be advisable to change the sequence of individual reaction steps so that certain by-products are not formed, or are formed in smaller amounts.

The reaction mixtures are generally worked up by methods known per se, for example by removing the solvent, partitioning the residue in a mixture of water and a suitable organic solvent, and working up the organic phase to obtain the product.

The benzylhydroxylamines of the formula I may contain one or more chiral centers and are then usually obtained in the form of enantiomer or diastereomer mixtures, unless the synthesis is tailored to yield one particular isomer. If desired, the mixtures can be separated by the methods customary for this purpose, for example by means of crystallization or chromatography on an optically active adsorbate, to give the essentially pure isomers. Pure optically active isomers can, for example, also be prepared from corresponding, optically active starting materials.

Benzylhydroxylamines I where $R^3$, $R^7$ or $R^8$ are hydrogen can be converted into their salts, preferably their alkali metal salts, in a manner known per se.

Salts of I whose metal ion is not an alkali metal ion can be prepared in the customary manner by double decomposition of the corresponding alkali salt, and ammonium, phosphonium, sulfonium and sulfoxonium salts by means of ammonia, phosphonium hydroxide, sulfonium hydroxide or sulfoxonium hydroxide.

The compounds I and their agriculturally useful salts, both in the form of isomer mixtures and in the form of the pure isomers, are suitable as herbicides. The herbicidal compositions comprising I effect very good vegetation control on non-crop areas, particularly at high application rates. They act against broad-leaved weeds and grass weeds in crops such as wheat, rice, maize, soya and cotton, without adversely affecting the crop plants to a substantial extent. This effect is particularly pronounced at low rates of application.

Depending on the application method in question, the compounds I, or the herbicidal compositions comprising them, can also be employed in a number of other crop plants for eliminating undesirable plants. Suitable crops are, for example, the following:

*Allium cepa, Ananas comosus, Arachis hypogaea, Asparagus officinalis, Beta vulgaris* spp. [sic] *altissima, Beta vulgaris* spp. [sic] *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus ssp., *Manihot esculenta, Medicago sativa,* Musa spp., *Nicotiana tabacum* (*N.rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* und *Zea mays.*

Moreover, the compounds I can also be used in crops which tolerate the action of herbicides as a result of breeding, including genetic engineering methods.

Furthermore, the benzylhydroxylamines I are also suitable for the desiccation and/or defoliation of plants.

As desiccants, they are particularly suitable for desiccating the aerial parts of crop plants such as potatoes, oilseed rape, sunflowers and soya beans. This allows completely mechanical harvesting of these important crop plants.

Also of economical interest is facilitating harvesting, which is made possible by concentrating, in the course of time, dehiscence or reducing the adhesion to the tree in the case of citrus fruit, olives or other species and varieties of pomaceous fruit, stone fruit and hard-shelled fruit. The same mechanism, i.e. promotion of the formation of abscission tissue between fruits or leaves and the shoot of the plants is also essential for the targeted defoliation of useful plants, in particular cotton.

Moreover, the reduced period of time within which the individual cotton plants mature results in better fiber quality post-harvest.

The compounds I, or the compositions comprising them, can be applied, for example, in the form of directly sprayable aqueous solutions, powders, suspensions, also highly concentrated aqueous, oily or other suspensions or dispersions, emulsions, oil dispersions, pastes, dusts, spreading materials or granules, by means of spraying, atomizing, dusting, scattering or pouring. The use forms depend on the intended purposes; in any case, they should guarantee the finest possible distribution of the active ingredients according to the invention.

Suitable inert auxiliaries for the preparation of directly sprayable solutions, emulsions, pastes or oil dispersions are, mainly, mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes or their derivatives, alkylated benzenes and their derivatives, alcohols, such as methanol, ethanol, propanol, butanol and cyclohexanol, ketones, such as cyclohexanone, strongly polar solvents, e.g. amines, such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substrates [sic], either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier, and, if desired, solvent or oil, and these concentrates are suitable for dilution with water.

Suitable surfactants (adjuvants) are the alkali metal salts, alkaline earth metal salts and ammonium salts of aromatic sulfonic acids, e.g. ligninsulfonic acid, phenolsulfonic acid, naphthalenesulfonic acid and dibutylnaphthalenesulfonic acid, or of fatty acids, alkyl- and alkylarylsulfonates, alkyl, lauryl ether and fatty alcohol sulfates, and salts of sulfated hexa-, hepta- and octadecanols, and also of fatty alcohol glycol ether [sic], condensates of sulfonated naphthalene and its derivatives with formaldehyde, condensates of naphthalene or of the naphthalenesulfonic acid with phenol and formaldehyde, olyoxyethylene octylphenol ether, ethoxylated isooctyl-, octyl- or nonylphenol, alkylphenyl polyglycol ethers, tributylphenyl olyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, spreading materials and dusts can be prepared by mixing or concomitantly grinding the active ingredients with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powder, or other solid carriers.

The concentrations of the active ingredients I in the ready-to-use preparations can be varied within wide limits. In general, the formulations comprise from 0.001 to 98% by weight, preferably 0.01 to 95% by weight, of at least one active ingredient. The active ingredients are employed in a purity of from 90% to 100%, preferably 95% to 100% (in accordance with NMR spectrum).

The formulation examples which follow illustrate the preparation of such products:

I. 20 parts by weight of compound No. It.10 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein leaves an aqueous dispersion comprising 0.02% by weight of the active ingredient.

II. 20 parts by weight of compound No. 1.02 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

III. 20 parts by weight of active ingredient No. 1.03 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

IV. 20 parts by weight of active ingredient No. 1.05 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

V. 3 parts by weight of active ingredient No. 1.04 are mixed with 97 parts by weight of finely divided kaolin. This gives a dust comprising 3% by weight of the active ingredient.

VI. 20 parts by weight of active ingredient No. 1.16 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of active ingredient No. 1.17 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of active ingredient No. 1.18 is dissolved in a mixture composed of 80 parts by weight of cyclohexanone and 20 parts by weight of Uniperol® EL (=non-ionic emulsifier based on ethoxylated castor oil). This gives a stable emulsion concentrate.

The active ingredients I or the herbicidal compositions comprising them can be applied pre- or post-emergence. If the active ingredients are less well tolerated by certain crop plants, application techniques may be used where the herbicidal compositions are sprayed, with the aid of the spraying apparatus, in such a manner that the active ingredients come into as little contact as possible with the leaves of the sensitive crop plants while reaching the leaves of undesirable plants which grow thereunder, or the naked soil surface (post-directed, lay-by).

Depending on the intended control target, the season, the target plants and the growth stage, the application rates of active ingredient I are from 0.001 to 3.0, preferably 0.01 to 1.0, kg of active ingredient (a.i.) per ha.

To widen the spectrum of action and to achieve synergistic effects, the benzylhydroxylamines I may be mixed with a large number of representatives of other groups of herbicidal or growth-regulating active ingredients and then applied concomitantly. Suitable components for mixtures are for example 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Furthermore, it may be advantageous to apply the compounds I, alone or in combination with other herbicides, together with other crop protection agents, for example with pesticides or agents for controlling phytopathogenic fungi or bacteria. Also of interest is the miscibility with mineral salt solutions, which are employed for treating nutrient and trace element deficiencies. Non-phytotoxic oils and oil concentrates may also be added.

PREPARATION EXAMPLES

Example 1

3-(4-Chloro-3-methoxyaminomethylphenyl)-1-methyl-6-trifluoromethyl-1,2,3,4-tetrahydropyrimidine-2,4-dione (compound No. 1.01)

Triethylsilane (1.9 ml) was added dropwise to a solution of 3-(4-chloro-3-methoxyiminomethylphenyl)-1-methyl-6-trifluoromethyl-1,2,3,4-tetrahydropyrimidine-2,4-dione (3.6 g) in a mixture of 30 ml of dichloromethane and 50 ml of trifluoroacetic acid. After the mixture had been stirred for 20 hours at room temperature, the solvent was distilled off. The residue was taken up in 200 ml of dichloromethane, whereupon the organic phase was washed four times using 50 ml of water in each case, dried over sodium sulfate and finally concentrated. Crystallization using diisopropyl ether and petroleum ether gave the title compound (m.p. 83–85° C.).

Example 2

3-(4-Chloro-3-ethoxyaminomethylphenyl)-1-methyl-6-trifluoromethyl-1,2,3,4-tetrahydropyrimidine-2,4-dione (compound No. 1.02)

Borane-pyridine complex (3 ml) and 10-percent hydrochloric acid (30 ml) were added dropwise in succession at 0° C. to a solution of 3-(4-chloro-3-ethoxyiminomethylphenyl)-1-methyl-6-trifluoromethyl-1,2,3,4-tetrahydropyrimidine-2,4-dione (3.8 g) in 40 ml of ethanol. In the course of 16 hours, another 12 ml of boranepyridine complex were added. The solution was subsequently stirred for 4 hours at reflux temperature, whereupon the solvent was distilled off. The residue was taken up in 200 ml of dichloromethane. The organic phase was washed twice using 50 ml of water in each case, then dried over sodium sulfate, and finally concentrated. This gave the title compound as an oil.

Example 3

3-(3-[Acetyl(methoxyamino)methyl]-4-chlorophenyl)-1-methyl-6-trifluoromethyl-1,2,3,4-tetrahydropyrimidine-2,4-dione (compound No. 1.04)

3-(4-Chloro-3-methoxyaminomethylphenyl)-1-methyl-6-trifluoroethyl-1,2,3,4-tetrahydropyrimidine-2,4-dione (1.6 g in 30 ml of tetrahydrofuran) was added dropwise to a suspension of sodium hydride (0.17 g in 50 ml of tetrahydrofuan [sic]). After one hour, acetyl chloride (0.4 g in 20 ml of tetrahydrofuran) was added. The mixture was stirred for 20 hours at room temperature and subsequently treated with water (100 ml). The desired product was extracted from the aqueous phase by using 2×100 ml of dichloromethane. The combined organic phases were washed three times using water, dried over sodium sulfate and freed from the solvent. Silica gel chromatography (eluent: dichloromethane/ethyl acetate 9:1) and crystallization using petroleum ether gave the title compound (m.p. 160–161° C.).

Example 4

3-(3-[(Methoxymethylamino)methyl]-4-chlorophenyl)-1-methyl-6-trifluoromethyl-1,2,3,4-tetrahydropyrimidine-2,4-dione (compound No. 1.06)

3-(3-Bromomethyl)-4-chloro-2-fluorophenyl)-1-methyl-6-trifluoromethyl-1,2,3,4-tetrahydropyrimidine-2,4-dione (0.005 mol) were added to a mixture of methoxyethylamine (0.06 mol), potassium carbonate (0.012 mol) and 100 ml of dimethylformamide. After 5 hours at room temperature, the reaction solution was concentrated. The residue was treated with 100 ml of methylene chloride, whereupon the organic phase was washed 3 times using 30 ml of water in each case, then dried over sodium sulfate and finally concentrated. The desired valuable product was obtained from the resulting oil by adding petroleum ether.

Example 5

3-(3-[Ethoxycarbonylaminooxymethyl]-4-chloro-6-fluorophenyl)-1-amino-6-trifluoromethyl-1,2,3,4-tetrahydropyrimidine-2,4-dione (Compound No. It.10)

0.9 g of carbonyldiimidazole was added to a solution of 1.8 g of 3-(3-hydroxymethyl-4-chloro-6-fluorophenyl)-1-amino-6-trifluoromethyl-1,2,3,4-tetrahydropyrimidine-2,4-dione in 100 ml of tetrahydrofuran. After the reaction mixture had been stirred for 1 hour, 0.58 g of N-ethoxycarbonylhydroxylamine was added. The mixture was subsequently stirred for a further 14 hours at 20° C. whereupon the solvent was removed by distillation. The residue was taken up in 100 ml of methylene chloride. The resulting organic phase was washed with water, dried over sodium sulfate and finally concentrated. The crude product was purified by means of chromatography on silica gel (eluent: methylene chloride). Yield: 0.2 g.

In addition to the compounds described above, other benzylhydroxylamines I which were, or can be, prepared by a similar method are listed in Table 4 below:

TABLE 4

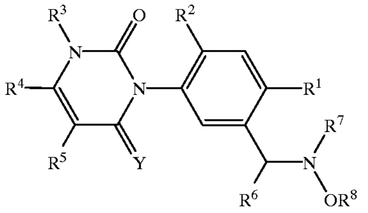

I

| No. | Y | R1 | $R^2$ | $R^3$ | $R^4$ | $R^5$ | $R^6$ | $R^7$ | $R^8$ | m.p. [° C.] |
|---|---|---|---|---|---|---|---|---|---|---|
| 1.01 | O | Cl | H | $CH_3$ | $CF_3$ | H | H | H | $CH_3$ | 83–85 |
| 1.02 | O | Cl | H | $CH_3$ | $CF_3$ | H | H | H | $C_2H_5$ | oil |
| 1.03 | O | Cl | H | $CH_3$ | $CF_3$ | H | H | $COOC_2H_5$ | $CH_3$ | oil |
| 1.04 | O | Cl | H | $CH_3$ | $CF_3$ | H | H | $COCH_3$ | $CH_3$ | 160–161 |
| 1.05 | O | Cl | F | $NH_2$ | $CF_3$ | H | H | H | $CH_3$ | 63–67 |
| 1.06 | O | Cl | H | $CH_3$ | $CF_3$ | H | H | $CH_3$ | $CH_3$ | |
| 1.07 | O | Cl | F | $NH_2$ | $CF_3$ | H | H | $CH_3$ | H | 153–155 |
| 1.08 | O | Cl | F | $NH_2$ | $CF_3$ | H | H | $COOCH_3$ | $CH_3$ | 112–115 |
| 1.09 | O | Cl | F | $NH_2$ | $CF_3$ | H | H | $COCH_3$ | $CH_3$ | 119–121 |
| 1.10 | O | Cl | F | $NH_2$ | $CF_3$ | H | H | $COCHCl_2$ | $CH_3$ | 122–125 |
| 1.11 | O | Cl | F | $NH_2$ | $CF_3$ | H | H | CO-cyclopropyl | $CH_3$ | 85–89 |
| 1.12 | O | Cl | F | $NH_2$ | $CF_3$ | H | H | $CH_3$ | $CH_3$ | oil |
| 1.13 | O | Cl | F | $NH_2$ | $CF_3$ | H | H | $COCH_2OCOCH_3$ | $CH_3$ | 90–94 |
| 1.14 | O | Cl | F | $NH_2$ | $CF_3$ | H | H | $COSCH_3$ | $CH_3$ | 113–120 |
| 1.15 | O | Cl | F | $NH_2$ | $CF_3$ | H | H | $COC_2H_5$ | $CH_3$ | 133–136 |
| 1.16 | O | Cl | F | $NH_2$ | $CF_3$ | H | H | $COOC_2H_5$ | $CH_3$ | 115–117 |
| 1.17 | O | Cl | F | $NH_2$ | $CF_3$ | H | H | $COCF_3$ | $CH_3$ | 162–164 |
| 1.18 | O | Cl | F | $NH_2$ | $CF_3$ | H | H | $CONH—C_6H_5$ | $CH_3$ | 138–143 |

USE EXAMPLES (Herbicidal Activity)

The herbicidal action of the benzylhydroxylamines I was demonstrated by the following greenhouse experiments:

The culture containers used were plastic flowerpots containing loamy sand with approximately 3.0% of humus as substrate. The seeds for the test plants were sown separately for each species.

In the case of the pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover results in uniform germination of the test plants, unless germination was adversely affected by the active ingredients.

For the post-emergence treatment, the test plants were first grown to a plant height of 3 to 15 cm, depending on the growth form, and only then treated with the active ingredients which were suspended or emulsified in water. The test plants were either sown directly and grown in the same containers, or were first grown separately as seedlings and transplanted to the test containers a few days prior to treatment. The rate of the application for the post-emergence treatment was 0.0156, 0.0078, 0.0039 or 0.0019 kg of a.i. (active ingredient) per ha.

The plants were kept at from 10 to 25° C. or 20 to 35° C., depending on the species. The test period extended to 2 to 4 weeks. During this time, the plants were tended, and their response to the individual treatments was evaluated.

The plants were scored using a scale from 0 to 100. 100 means no emergence of the plants, or complete destruction of at least the aerial parts, and 0 means no damage, or normal course of growth.

The plants used in the greenhouse experiments were of the following species:

| Scientific Name | English Name |
|---|---|
| *Abutilon theophrasti* | Velvet leaf |
| *Galium aparine* | Catchweed bedstraw |
| *Sinapis alba* | White mustard |
| *Solanum nigrum* | Black nightshade |
| Veronica subspecies | Speedwell |

At a rate of application of 0.0156 or 0.0078 kg of a.i./ha, compound No. 1.03 was very effective against *Abutilon theophrasti, Solanum nigrum* and various Veronica species when used post-emergence.

At a rate of application of 3.9 or 1.9 g of a.i./ha, compound No. It.10 was very effective against *Galium aparine, Sinapis alba* and *Solanum nigrum* when used post-emergence.

USE EXAMPLES (Desiccant/defoliant Activity)

The test plants used were young cotton plants with 4 leaves (without cotyledons), which had been grown under greenhouse conditions (relative atmospheric humidity 50 to 70%; day/night temperature=27/20° C.).

The young cotton plants were given foliar treatments to runoff point using the aqueous preparations of the active ingredients (with an addition of 0.15% by weight of the fatty alcohol alkoxylate Plurafac LF 700, based on the spray mixture). The amount of water applied was 1000 1/ha (converted). After 13 days, the number of shed leaves and the degree of defoliation in % were determined.

No leaves were shed by the untreated control plants.

We claim:

1. A benzylhydroxylamine of the formula I

I

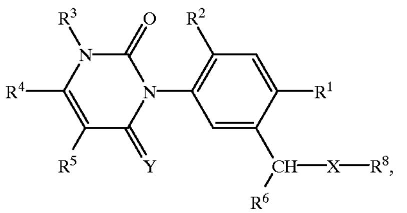

in which the variables have the following meanings:

X is —N($R^7$)—O— which can be bonded to $R^8$ via oxygen or nitrogen;

Y is oxygen or sulfur;

$R^1$ is halogen, cyano, nitro or trifluoromethyl;

$R^2$ is hydrogen or halogen;

$R^3$ is hydrogen, amino or methyl;

$R^4$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;

$R^5$ is hydrogen, halogen or $C_1$–$C_6$-alkyl;

$R^6$ is hydrogen, $C_1$–$C_6$-alkyl, $C_1$–$C_6$-haloalkyl, $C_3$–$C_6$-cycloalkyl or $C_2$–$C_6$-alkenyl;

$R^7$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_2$–$C_6$-alkenyloxy) carbonyl, ($C_2$–$C_6$-alkynyloxy) carbonyl, ($C_1$–$C_6$-alkylthio)carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$cycloalkoxy, $C_3$–$C_6$-alkenyloxy, $C_3$–$C_6$-alkynyloxy, $C_1$–$C_6$-alkoxy-$C_3$–$C_6$-alkoxy, $C_1$–$C_6$-alkylthio, ($C_1$–$C_6$-alkyl) carbonyl, ($C_1$–$C_6$-alkyl) carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^1R^9$, —OCO—$Z^1R^9$ or —N($R^9$)$R^{10}$, or $R^7$ is $C_3$–$C_8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_3$–$C_6$-alkyl, $C_1$–$C_6$-alkoxy and $C_1$–$C_6$-haloalkyl;

$R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, where each of the last-mentioned 5 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^2R^{11}$, —OCO—$Z^2R^{11}$ or —N($R^{11}$)$R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy, or an agriculturally useful salt of a compound I where $R^3$, $R^7$ and/or $R^8$ is hydrogen.

2. A benzylhydroxylamine of the formula I as claimed in claim 1, where the variables have the following meanings:

Y is oxygen;

$R^1$ is halogen or cyano;

$R^2$ is hydrogen, fluorine or chlorine;

$R^3$ is amino or methyl;

$R^4$ is $C_1$–$C_6$-alkyl, $C_1$–$C_6$-haloalkyl or $C_1$–$C_6$-alkylsulfonyl;

$R^5$ is hydrogen or halogen;

$R^6$ is hydrogen or $C_1$–$C_4$-alkyl;

$R^7$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$- alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_2$–$C_6$-alkenyloxy) carbonyl, ($C_2$–$C_6$-alkynyloxy)carbonyl, ($C_1$–$C_6$-alkylthio)carbonyl, $C_1$–$C_6$-alkylcarbamoyl, where each of the last mentioned 13 radicals is unsubstituted or carries one or two substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, and a group —CO—$Z^1R^9$, —OCO—$Z^1R^9$ or —N($R^9$)$R^{10}$, $R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, where each of the last-mentioned 5 radicals is unsubstituted or carries one or two substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, and a group —CO—$Z^2R^{11}$, —OCO—$Z^2R^{11}$ or —N($R^{11}$)$R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl or ($C_1$–$C_6$-alkoxy)carbonyl-$C_1$–$C_6$-alkyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen or $C_1$–$C_6$-alkyl.

3. A herbicidal composition comprising a herbicidally active amount of at least one benzylhydroxylamine of the formula I or at least one agriculturally useful salt of I as defined in claim 1 and at least one inert liquid or solid carrier and optionally at least one surfactant.

4. A composition for the desiccation and/or defoliation of plants, comprising an amount of at least one benzylhydroxylamine of the formula I or at least one agriculturally useful salt of I as defined in claim 1 which has a desiccant or defoliant action and at least one inert liquid or solid carrier and optionally at least one surfactant.

5. A process for the preparation of herbicidally active compositions, which comprises mixing a herbicidally active amount of at least one benzylhydroxylamine of the formula I or at least one agriculturally useful salt of I as defined in claim 1 and at least one inert liquid or solid carrier and optionally at least one surfactant.

6. A process for the preparation of a composition having a desiccant and/or defoliant action, which comprises mixing an amount of at least one benzylhydroxylamine of the formula I or at least one agriculturally useful salt of I as defined in claim 1 which has a desiccant or defoliant action and at least one inert liquid or solid carrier and optionally at least one surfactant.

7. A method of controlling undesirable vegetation, which comprises allowing a herbicidally active amount of at least one benzylhydroxylamine of the formula I or at least one agriculturally useful salt of I as defined in claim 1 to act on plants, their environment or on seed.

8. A method for the desiccation and/or defoliation of plants, which comprises allowing an amount of at least one benzylhydroxylamine of the formula I or at least one agriculturally useful salt of I as defined in claim 1 which has a desiccant or defoliant action to act on plants.

9. An enamine ester of the formula IV

IV

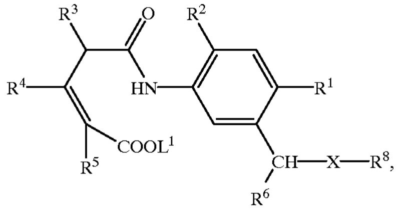

where $L^1$ is $C_1$–$C_6$-alkyl or phenyl and

X is —N($R^7$)—O— which can be bonded to $R^8$ via oxygen or nitrogen;

Y is oxygen or sulfur:

$R^1$ is halogen, cyano, nitro or trifluoromethyl;

$R^2$ is hydrogen or halogen;

$R^3$ is hydrogen, amino or methyl;

$R^4$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;

$R^5$ is hydrogen, halogen or $C_1$–$C_5$-alkyl;

$R^6$ is hydrogen, $C_1$–$C_6$-alkyl, $C_1$–$C_6$-haloalkyl, $C_3$-$C_6$-cycloalkyl or $C_1$–$C_6$-alkenyl;

$R^7$ is hydrogen, $C_1$–$C_6$-alkyl, $C_3C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_2$–$C_6$-alkenyloxy)carbonyl, ($C_2$–$C_6$-alkynyloxy)carbonyl, ($C_1$–$C_6$-alkylthio)carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$-$C_8$cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl)carbonyl, ($C_1$–$C_6$-alkyl)carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl) carbonyl, a group —CO—$Z^1R^9$, —OCO—$Z^1R^9$ or —N($R^9$)$R^{10}$, or $R^7$ is $C_3$–$C_8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_1$–$C_6$-alkyl, $C_1$–$C_6$-alkoxy and $C_1$–$C_6$ -haloalkyl;

$R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, where each of the last-mentioned 5 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^2R^{11}$, —OCO—$Z^2R^{11}$ or —N($R^{11}$) $R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy.

10. An enamine carboxylate of the formula V

V

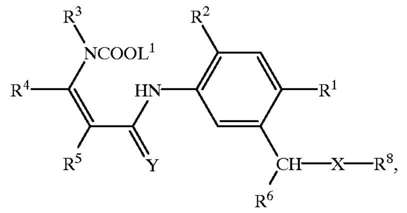

where $L^1$ is $C_1$–$C_6$-alkyl or phenyl and

X is —N($R^7$)—O— which can be bonded to $R^8$ via oxygen or nitrogen;

Y is oxygen or sulfur;

$R^1$ is halogen, cyano, nitro or trifluoromethyl;

$R^2$ is hydrogen or halogen;

$R^3$ is hydrogen, amino or methyl;

$R^4$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;

$R^5$ is hydrogen, halogen or $C_1$–$C_6$-alkyl;

$R^6$ is hydrogen, $C_1$–$C_6$-alkyl, $C_1$–$C_6$-haloalkyl, $C_3$–$C_6$-cycloalkyl or $C_2$–$C_6$-alkenyl;

$R^7$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl carbonyl, ($C_3$–$C_6$-alkenyl)carbonyl, ($C_3$–$C_6$-alkynyl)carbonyl, ($C_1$–$C_6$-alkoxy)carbonyl, ($C_2$–$C_6$-alkenyloxy)carbonyl, $C_2$–$C_6$-alkynyloxy)carbonyl, ($C_1$–$C_6$-alkylthio) carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl hydroxyl, $C_1$–$C_6$-alkoxy, $C_3$–$C_8$cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl) carbonyl, ($C_1$–$C_6$-alkyl) carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_5$-haloalkyl and ($C_1$–$C_6$-alkyl) carbonyl, a group —CO—$Z^1R^9$, —OCO—$Z^1R^9$ or —N($R^9$)$R^{10}$, or $R^7$ is $C_3$–$C_8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl;

$R^8$ is hydrogen, $C_1$–$C_6$-alkyl, $C_1$–$C_6$-cycloalkyl, $C_1$–$C_6$-haloalkyl, $C_3$–$C_6$-alkenyl or $C_3$–$C_6$-alkynyl, where each of the last-mentioned 5 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^2R^{11}$, —OCO—$Z^2R^{11}$ or —N($R^{11}$)$R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy.

11. A phenylurea derivative of the formula XIII

XIII

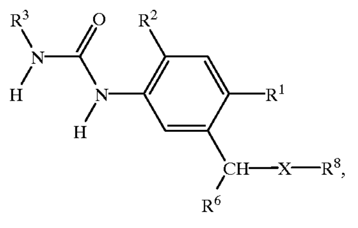

where

X is —N($R^7$)—O— which can be bonded to $R^8$ via oxygen or nitrogen;

$R^1$ is halogen, cyano, nitro or trifluoromethyl;

$R^2$ is hydrogen or halogen;

$R^3$ is hydrogen, amino or methyl;

$R^6$ is hydrogen, $C_1$–$C_6$-alkyl, $C_1$–$C_6$-haloalkyl, $C_3$–$C_6$-cycloalkyl or $C_2$–$C_6$-alkenyl;

$R^7$ is hydrogen, $C_1$–$C_6$-alkyl, $C_1$–$C_6$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_1$–$C_6$-alkenyloxy) carbonyl, ($C_2$–$C_6$-alkynyloxy)carbonyl, ($C_1$–$C_6$-alkylthio) carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl) carbonyl, ($C_1$–$C_6$-alkyl) carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^1R^9$, —OCO—$Z^1R^9$ or —N($R^9$)$R^{10}$, or $R^7$ is $C_3$–$C_8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl;

$R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, where each of the last-mentioned 5 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and $C_1$–$C_6$-alkyl) carbonyl, a group —CO—$Z^2R^{11}$, —OCO—$Z^2R^{11}$ or —$N(R^{11})R^{12}$;

$Z^1$ is a chemical bond, oxygen, sulfur or —$N(R^{10})$—;

$Z^2$ is a chemical bond, oxygen, sulfur or —$N(R^{12})$—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy )carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy.

12. A phenylisocyanate of the formula XVI

XVI

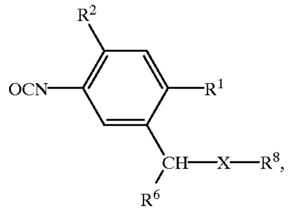

where

X is —$N(R^7)$—O— which can be bonded to $R^8$ via oxygen or nitrogen;

$R^1$ is halogen, cyano, nitro or trifluoromethyl;

$R^2$ is hydrogen or halogen;

$R^6$ is hydrogen, $C_1$–$C_6$-alkyl, $C_1$–$C_6$-haloalkyl, $C_3$–$C_6$-cycloalkyl or $C_2$–$C_6$-alkenyl;

$R^7$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl carbonyl, ($C_3$–$C_6$-alkenyl)carbonyl, ($C_3$–$C_6$-alkynyl carbonyl, ($C_1$–$C_6$-alkoxy)carbonyl, ($C_2$–$C_6$-alkenyloxy)carbonyl, ($C_2$–$C_6$-alkynyloxy carbonyl, ($C_1$–$C_6$-alkylthio)carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl) carbonyl, ($C_1$–$C_6$-alkyl) carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^1R^9$, —OCO—$Z^1R^9$ or —$N(R^9)R^{10}$, or $R^7$ is $C_3$–$C_8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl;

$R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, where each of the last-mentioned 5 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl) carbonyl, a group —CO—$Z^2R^{11}$, —OCO—$Z^2R^{11}$ or —$N(R^{11})R^{12}$;

$Z^1$ is a chemical bond, oxygen, sulfur or —$N(R^{10})$—;

$Z^2$ is a chemical bond, oxygen, sulfur or —$N(R^{12})$—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_5$-alkoxy)carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy.

13. An aniline derivative of the formula XVII

XVII

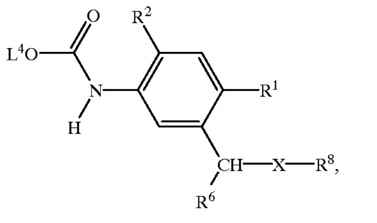

where $L^4$ is $C_1$–$C_4$-alkyl or phenyl and

X is —N($R^7$)—O— which can be bonded to $R^8$ via oxygen or nitrogen;

$R^1$ is halogen, cyano, nitro or trifluoromethyl;

$R^2$ is hydrogen or halogen;

$R^6$ is hydrogen, $C_1$–$C_6$-alkyl, $C_1$–$C_6$-haloalkyl, $C_3$–$C_6$-cycloalkyl or $C_2$–$C_6$-alkenyl;

$R^7$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_1$–$C_6$-alkenyloxy)carbonyl, ($C_1$–$C_6$-alkynyloxy)carbonyl, ($C_1$–$C_6$-alkylthio) carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl) carbonyl, ($C_1$–$C_6$-alkyl) carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl) carbonyl, a group —CO—$Z^1R^9$, —OCO—$Z^1R^9$ or —N($R^9$)$R^{10}$, or $R^7$ is $C_3$–$C_8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl;

$R^8$ is hydrogen, $C_1$–$C_6$-alkyl, $C_3$–$C_8$-cycloalkyl, $C_1$–$C_6$-haloalkyl, $C_3$–$C_6$-alkenyl or $C_3$–$C_6$-alkynyl, where each of the last-mentioned 5 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^2R^{11}$, —OCO—$Z^2R^{11}$ or —N($R^{11}$)$R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl $C_1$–$C_6$-alkyl, $C_3$–$C_8$-cycloalkyl or $C_1$–$C_6$-alkoxy.

14. An aniline compound of the formula XIX

XIX

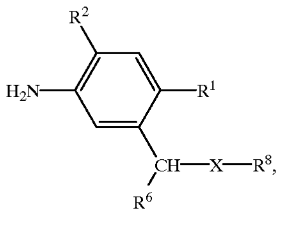

where

X is —N($R^7$)—O— which can be bonded to $R^8$ via oxygen or nitrogen;

$R^1$ is halogen, cyano, nitro or trifluoromethyl;

$R^2$ is hydrogen or halogen;

$R^6$ is hydrogen, $C_1$–$C_6$-alkyl, $C_3$–$C_8$-haloalkyl, $C_1$–$C_6$-cycloalkyl or $C_2$–$C_6$-alkenyl;

$R^7$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_2$–$C_6$-alkynyl)carbonyl, ($C_3$–$C_6$-alkoxy)carbonyl, ($C_2$–$C_6$-alkenyloxy) carbonyl, ($C_2$–$C_6$-alkynyloxy)carbonyl, ($C_1$–$C_6$-alkylthio)carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl) carbonyl, ($C_1$–$C_6$-alkyl)carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl) carbonyl, a group —CO—$Z^1R^9$, —OCO—$Z^1R^9$ or —N($R^9$)$R^{10}$, or $R^7$ is $C_1$–$C^8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl;

$R^8$ is hydrogen, $C_3$–$C_8$-cycloalkyl, $C_1$–$C_6$-haloalkyl, $C_3$–$C_6$-alkenyl or $C_3$–$C_6$-alkynyl, where each of the last-mentioned 4 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl) carbonyl, a group —CO—$Z^2R^{11}$, —OCO—$Z^2R^{11}$ or —N($R^{11}$) $R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy.

15. A nitro compound of the formula XXIII

XXIII

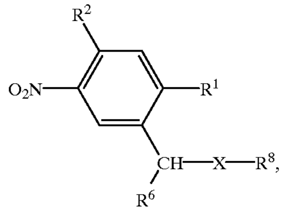

where

X is —N($R^7$)—O— which can be bonded to $R^8$ via oxygen or nitrogen;

$R^1$ is halogen, cyano, nitro or trifluoromethyl;

$R^2$ is hydrogen or halogen;

$R^6$ is hydrogen, $C_1$–$C_6$-alkyl, $C_1$–$C_6$-haloalkyl, $C_3$–$C_6$-cycloalkyl or $C_2$–$C_6$-alkenyl;

$R^7$ is hydrogen, $C_1$–$C_6$-alkyl, $C_4$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl, ($C_1$–$C_6$-alkoxy)carbonyl, ($C_2$–$C_6$-alkenyloxy) carbonyl, ($C_2$–$C_6$-alkynyloxy) carbonyl, ($C_1$–$C_6$-alkylthio) carbonyl, $C_1$–$C_6$-alkylsulfonyl, $C_1$–$C_6$-alkylcarbamoyl, where each of the last mentioned 14 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$cycloalkoxy $C_3$–$C_6$-alkenyloxy $C_3$–$C_6$-alkynyloxy, $C_1$–$C_6$-alkoxy-$C_1$–$C_6$-alkoxy, $C_1$–$C_6$-alkylthio, ($C_1$–$C_6$-alkyl) carbonyl, ($C_1$–$C_6$-alkyl)carbonyloxy, $C_1$–$C_6$-alkylsulfinyl, $C_1$–$C_6$-alkylsulfonyl, $C_1$–$C_6$-alkylideneaminoxy, $C_1$–$C_6$-alkylcarbamoyl, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$Z^1R^9$, —OCO—$Z^1R^9$ or —N($R^9$)$R^{10}$, or $R^7$ is $C_3$–$C_8$-cycloalkylcarbonyl, phenylcarbonyl, phenylsulfonyl or phenylcarbamoyl, where these 4 radicals are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl;

$R^8$ is hydrogen, $C_3$–$C_8$-cycloalkyl, $C_1$–$C_6$-haloalkyl, $C_3$–$C_6$-alkenyl or $C_3$–$C_6$-alkynyl, where each of the last-mentioned 4 radicals is unsubstituted or carries one to three substituents selected from the group consisting of nitro, cyano, halogen, $C_3$–$C_8$-cycloalkyl, hydroxyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy or phenylsulfonyl, where the phenyl rings are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms, selected from the group consisting of two oxygen atoms, two sulfur atoms and 3 nitrogen atoms, where the heterocycle is saturated, partially or fully unsaturated or aromatic, and, where the heterocycle is unsubstituted or carries one to three substituents selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl) carbonyl, a group —CO—$Z^2R^{11}$, —OCO—$Z^2R^{11}$ or —N($R^{11}$) $R^{12}$;

$Z^1$ is a chemical bond, oxygen, sulfur or —N($R^{10}$)—;

$Z^2$ is a chemical bond, oxygen, sulfur or —N($R^{12}$)—;

$R^9$, $R^{11}$ independently of one another are hydrogen, $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, where the phenyl and the phenyl ring of the phenylalkyl group is unsubstituted or carries one to three radicals selected from the group consisting of nitro, cyano, halogen, $C_1$–$C_6$-alkyl, $C_1$–$C_6$-haloalkyl, $C_1$–$C_6$-alkoxy or ($C_1$–$C_6$-alkyl)carbonyl, or $Z^1$ and $R^9$ and/or $Z^2$ and $R^{11}$ in each case together are a 3- to 7-membered heterocycle bonded via nitrogen and having one to three hetero atoms selected from the group consisting of two oxygen atoms, two sulfur atoms and 3 nitrogen atoms, where the heterocycle is saturated, partially or fully unsaturated or aromatic and where the heterocycle is unsubstituted or carries one to three substituents selected from the group consisting of nitro, cyano, halogen, $C_1$–$C_6$-alkyl, $C_1$–$C_6$-haloalkyl and $C_1$–$C_6$-alkoxy;

$R^{10}$, $R^{12}$ independently of one another are hydrogen, hydroxyl, $C_1$–$C_6$-alkyl, $C_3$–$C_8$-cycloalkyl or $C_1$–$C_6$-alkoxy.

* * * * *

UNITED STATES PATENT AND TRADEMARK OFFICE

CERTIFICATE OF CORRECTION

PATENT NO. : 6,057,269
DATED : May 2, 2000
INVENTOR(S) : Klintz et al.

It is certified that error appears in the above-identified patent and that said Letters Patent is hereby corrected as shown below:

In the Abstract:
Page 1, last line after "$Z^1$" insert -- = --.

Column 45:
Line 41, change "$C_3$" to -- $C_1$ --.

Column 48:
Line 41, change "$C_1$" to -- $C_2$

Column 50:
Line 36, after "cycloalkyl" insert a comma --,--.
Line 66, change "$C_1$-$C_6$" (second occurrence) to --$C_3$-$C_8$--.

Column 52:
Line 5, change " "$C_1$-$C_6$" (second occurrence) to --$C_3$-$C_8$--.
Line 8, change "$C_1$-$C_6$" (second occurrence) to --$C_2$-$C_6$--.

Column 55:
Line 32, change "$C_1$" (second occurrence) to --$C_2$--.
Line 33, change "$C_1$" to --$C_2$--.

UNITED STATES PATENT AND TRADEMARK OFFICE
CERTIFICATE OF CORRECTION

PATENT NO. : 6,057,269
DATED : May 2, 2000
INVENTOR(S) : Klintz et al.

It is certified that error appears in the above-identified patent and that said Letters Patent is hereby corrected as shown below:

Column 57:
Line 3, change "$C_3$-$C_8$-haloalkyl, $C_1$-$C_6$" to --$C_1$-$C_6$-haloalkyl, $C_3$-$C_6$ --.
Line 5, change "$C_1$-$C_6$" to --$C_3$-$C_8$--.
Line 7, change "$C_2$" to --$C_3$--.
Line 8, change "$C_3$" to --$C_1$--.

Column 58:
Line 50, change "$C_4$" to --$C_3$--.

Signed and Sealed this

Seventh Day of August, 2001

*Attest:*

Nicholas P. Godici

NICHOLAS P. GODICI

*Attesting Officer*

*Acting Director of the United States Patent and Trademark Office*